US00RE43067E

(19) United States
(12) Reissued Patent
Yoshitomo et al.

(10) Patent Number: US RE43,067 E
(45) Date of Reissued Patent: Jan. 3, 2012

(54) METHOD FOR PRODUCING NEW POLYNUCLEAR POLY(FORMYLPHENOL)

(75) Inventors: Akira Yoshitomo, Wakayama (JP); Tatsuya Iwai, Wakayama (JP); Kentaro Watanabe, Wakayama (JP)

(73) Assignee: Honshu Chemical Industry Co., Ltd., Tokyo (JP)

(21) Appl. No.: 12/984,215

(22) Filed: Jan. 4, 2011

Related U.S. Patent Documents

Reissue of:

(64) Patent No.: 7,750,190
Issued: Jul. 6, 2010
Appl. No.: 12/299,902
PCT Filed: May 31, 2007
PCT No.: PCT/JP2007/061107
§ 371 (c)(1),
(2), (4) Date: Dec. 3, 2008
PCT Pub. No.: WO2007/139191
PCT Pub. Date: Dec. 6, 2007

(30) Foreign Application Priority Data

May 31, 2006 (JP) ..... 2006-151973
Jun. 9, 2006 (JP) ..... 2006-161694

(51) Int. Cl.
*C07C 45/00* (2006.01)

(52) U.S. Cl. ..... 568/426; 568/433; 568/436; 568/442

(58) Field of Classification Search ..... None
See application file for complete search history.

(56) References Cited

U.S. PATENT DOCUMENTS

| | | | | |
|---|---|---|---|---|
| 3,833,660 | A * | 9/1974 | Smith | 568/436 |
| 7,456,323 | B2 * | 11/2008 | Yoshitomo et al. | 568/436 |
| 7,586,009 | B2 * | 9/2009 | Yoshitomo et al. | 568/433 |

FOREIGN PATENT DOCUMENTS

| | | |
|---|---|---|
| JP | 52-136141 | 11/1977 |
| JP | 05-125032 | 5/1993 |
| JP | 05-339191 | 12/1993 |
| JP | 07-061948 | 3/1995 |
| JP | 2002-193872 | 7/2002 |
| JP | 2003-300922 | 10/2003 |
| WO | WO 2004/050231 A3 | 6/2004 |

OTHER PUBLICATIONS

Kim et al., Synthesis of Calixsalen: A Route to Azacalixarene Analogue, Bull. Korean Chem. Soc., Feb. 2007, vol. 28, No. 2, pp. 315-318.*

Giovanni Casiraghi, et al., "Selective Reactions using Metal Phenoxides. Part 1. Reactions with Formaldehyde," J. Chem. Soc., Perkin Trans., pp. 318-321, 1862-1865, 1978.

Maeng, Ki Suck, et al., "Methylene-bis-salicyl aldehyde," Chungnam National University Industrial Technology Lab Papers vol. 4, No. 2, pp. 124-130.

J.B. Fontecha, et al., Dinuclear complexes of a pseudocalixarene macrocycle: structural consequences of intramolecular hydrogen bonding, Dalton Transactions, No. 5, pp. 923-929, 2005 Experimental.

* cited by examiner

*Primary Examiner* — Rosalynd Keys
(74) *Attorney, Agent, or Firm* — Knobbe Martens Olson & Bear LLP

(57) ABSTRACT

Produce the target substance, or a polynuclear poly (formylphenol) expressed by General Formula (2), in an industrial setting with ease and at high purity by causing a polynuclear poly(hydroxymethylphenol) or polynuclear poly (alkoxymethylphenol) to react with hexamethylene tetramine in the presence of an acid and then hydrolyzing the obtained reaction product.

7 Claims, No Drawings

METHOD FOR PRODUCING NEW POLYNUCLEAR POLY(FORMYLPHENOL)

Matter enclosed in heavy brackets [ ] appears in the original patent but forms no part of this reissue specification; matter printed in italics indicates the additions made by reissue.

This application is the U.S. National Phase under 35 U.S.C. §371 of International Application PCT/JP2007/061107, filed May 31, 2007, which claims priority to Japanese Patent Application No. 2006-151973, filed May 31, 2006, and No. 2006-161694, filed Jun. 9, 2006. The International Application was published under PCT Article 21(2) in a language other than English.

TECHNICAL FIELD

The present invention relates to a method for producing a polynuclear poly(formylphenol) in an industrial setting with ease and at high purity. To be specific, the present invention relates to a method for producing a polynuclear poly (formylphenol) in an industrial setting with ease and at high yield and high purity by using as the material a polynuclear poly(hydroxymethylphenol) or polynuclear poly(alkoxymethylphenol) that can be obtained easily from a polynuclear polyphenol, and causing the material to react with hexamethylene tetramine in the presence of an acid and then hydrolyzing the obtained reaction product.

PRIOR ART

Traditionally, the Reimer-Tiemann reaction that uses chloroform and aqueous sodium hydroxide solution, as well as the Duff reaction that uses hexamethylene tetramine and an acid catalyst such as trifluoroacetate, are known as ways to introduce a formyl group to a phenol. These methods are both based on a reaction to directly introduce a formyl group to a phenyl nucleus by means of substitution, where the former method uses a large amount of halogenated hydrocarbon and provides a low yield, while the latter method, based on an examination by the inventors for the present invention, in many cases is unable to synthesize the target substance at a high yield even when applied to a polynuclear phenol as shown in a comparative example included in the present application for patent, or requires a very long reaction time.

Also, a method to cause a given amount of phenol to react with the same amount of alkyl magnesium bromide and then cause the obtained reaction product to react with formaldehyde to achieve formylation is described in J. Chem. Soc., Perkin Trans. (1978, 318 to 321). However, this method has a drawback of requiring a large amount of expensive alkyl magnesium bromide.

A method to cause a phenol to react with tin tetrachloride and then cause the obtained reaction product to react with formaldehyde to achieve formylation is described in J. Chem. Soc., Perkin Trans. (1978, 1862 to 1865). However, this method uses a large amount of expensive tin tetrachloride and also requires treatment of a large amount of wastewater generated from the reaction, which is undesirable. Also in this literature, a salicylaldehyde is synthesized from tin tetrachloride by also using 2-hydroxy benzyl alcohol. However, an examination by the inventors for the present application found that this method could not be applied favorably to a polynuclear polyphenol.

A method to oxidize a hydroxy methyl phenol to produce a hydroxy methyl benzaldehyde is described in Japanese Patent Laid-open No. 52-136141. However, this method is based on a gas/liquid reaction and therefore the reaction yield changes easily according to the agitation condition, etc. Also, pure oxygen is used, which makes it difficult to use this method in an industrial setting.

On the other hand, among the various methods to synthesize a bis(formylphenol) or polynuclear poly(formylphenol), a method to cause salicylaldehyde and formaldehyde to react with each other using an acid catalyst is described in Chungnam National University Industrial Technology Lab Papers Vol. 4, No. 2 (1977). However, the substituted benzaldehyde, which is used as the material, is expensive and if the reaction uses a carbonyl compound other than formaldehyde, the low reactivity causes benzaldehyde itself to polymerize under conditions where the carbonyl compound undergoes reaction. These factors make it difficult to apply this method.

Also, a method to tetraformylate a bisphenol is described in Toku-Kai-Hei 5-125032. However, the yield is low and, because a large amounts of hexamethylene tetramine and acid are used compared to the bisphenol, the volumetric efficiency is poor and therefore this method cannot be implemented in an industrial setting.

Furthermore, a method to cause 5-iodine-3-tert-butyl salicylaldehyde and 1,3,5-triethynyl benzene with each other in the presence of bis(triphenolphosphine)palladium, iodinated copper and triethyl amine to obtain 1,3,5-tris[(5-tert-butyl-3-formyl-4-hydroxyphenyl)ethynyl]benzene is described in WO Laid-open No. 2004/050231. However, this method uses expensive materials.

As explained above, it was difficult under any conventional method to produce a polynuclear formyl phenol in an industrial setting with ease and at high yield and high purity.

| | |
|---|---|
| Patent Literature 1: | Japanese Patent Laid-open No. Sho 52-136141 |
| Patent Literature 2: | Japanese Patent Laid-open No. Hei 5-125032 |
| Patent Literature 3: | WO Laid-open No. 2004/050231 |
| Non-patent Literature 1: | J. Chem. Soc., Perkin Trans. (1978, 318 to 321, 1862 to 1865) |
| Non-patent Literature 2: | Chungnam National University Industrial Technology Lab Papers Vol. 4, No. 2 (1977) |

SUMMARY OF THE INVENTION

Problems to be Solved by the Invention

The present invention relates to a method for producing a polynuclear formyl phenol in an industrial setting with ease and at high yield and high purity. To be specific, the present invention relates to a method for producing a polynuclear formyl phenol by using as the material a polynuclear poly (hydroxymethylphenol) or polynuclear poly(alkoxymethylphenol) that can be obtained easily from a polynuclear polyphenol.

Means for Solving the Problems

After examining diligently to achieve the aforementioned purpose, the inventors found that the desired polynuclear formyl phenol could be obtained at high yield as a bis (formylphenol) or a polynuclear poly(formylphenol) having three or more hydroxy-substituted phenol nuclei, by using as the direct material a hydroxymethyl-substituted or alkoxymethyl-substituted bisphenol or polynuclear poly(hydroxymethylphenol) or polynuclear poly(alkoxymethylphenol) that can be obtained easily by, for example, methylolation of a polynuclear polyphenol being a subject of the present invention, such as a bisphenol or a polynuclear polyphenol having three or more hydroxy-substituted phenol nuclei, and then causing the material to react with hexamethylene tetramine in the presence of an acid, followed by hydrolyzation of the obtained reaction product to convert into a formyl group the hydroxy methyl group or alkoxy methyl group substituted to the phenyl nucleus. Based on the above findings, the inventors completed the present invention.

To be specific, the present invention provides a method for producing a polynuclear poly(formylphenol) expressed by General Formula (2), wherein said method is characterized in that a polynuclear polyphenol expressed by General Formula (1) is caused to react with hexamethylene tetramine in the presence of an acid and then the reaction product is hydrolyzed.

General Formula (1)

[Chemical 1]

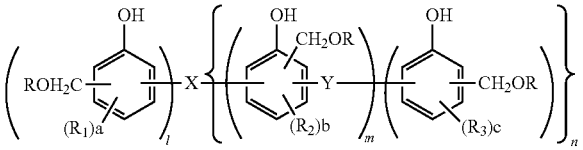

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an] ether group. $R_1$, $R_2$ and $R_3$ may be the same or different and respectively represent a hydrocarbon group, hydrocarbon group containing oxygen atom, hydroxyl group, halogen group or halogenated hydrocarbon group; a and c respectively indicate an integer of 0 or 1 to 3, while b indicates an integer of 0, 1 or 2; l and n respectively indicate an integer of 1 to 3; m indicates an integer of 0, 1 or 2; X indicates a bond group or single bond; and Y indicates a bivalent alkylene group.)

General Formula (2)

[Chemical 2]

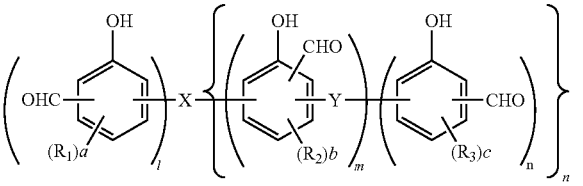

(In the formula, $R_1$, $R_2$, $R_3$, a, b, c, l, m, n, X, and Y indicate the same things represented by the corresponding symbols in General Formula (1).)

With a polynuclear polyphenol expressed by the aforementioned General Formula (1), if m is 0, X is a bivalent bond group or a single bond, and l+n is 2 in the formula, then a method for producing a polynuclear poly(formylphenol), wherein the polynuclear polyphenol is a bisphenol expressed by General Formula (3) specified below, and wherein similarly the polynuclear poly(formylphenol) expressed by the aforementioned General Formula (2) is a bis(formylphenol) expressed by General Formula (4) specified below, is a favorable embodiment of the present invention.

General Formula (3)

[Chemical 3]

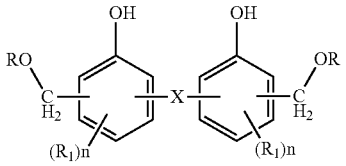

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an] ether group, where n indicates an integer of 0 or 1 to 3. Both $R_1$s may be the same or different and respectively represent a hydrocarbon group, hydrocarbon group containing oxygen atom, halogenated hydrocarbon group, hydroxyl group or halogen group. X indicates a bivalent bond group or a single bond.)

General Formula (4)

[Chemical 4]

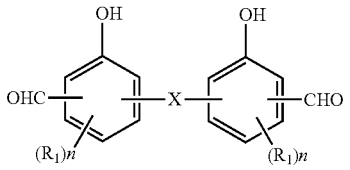

(In the formula, $R_1$, n and X indicate the same things represented by the corresponding symbols in General Formula (3).)

Also, a method for producing a polynuclear poly (formylphenol), wherein said method is characterized in that a bis(hydroxymethylphenol) expressed by General Formula (6), being a bisphenol expressed by the aforementioned General Formula (3) where R is a hydrogen atom, is obtained by causing a bisphenol expressed by General Formula (5) to react with formaldehyde in the presence of an alkali catalyst, is a favorable embodiment of the present invention.

General Formula (5)

[Chemical 5]

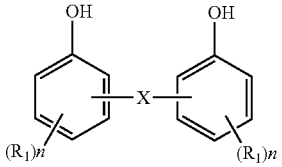

(In the formula, $R_1$, n and X indicate the same things represented by the corresponding symbols in General Formula (3), and at least one of the o-position and p-position of the hydroxyl group is not substituted.)

General Formula (6)

[Chemical 6]

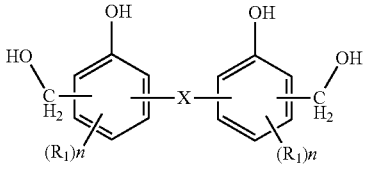

(In the formula, $R_1$, n and X indicate the same things represented by the corresponding symbols in General Formula (3), and the substitution position of the hydroxymethyl group corresponds to the o-position or p-position relative to the hydroxyl group.)

A method for producing a polynuclear poly(formylphenol) according to an embodiment of the present invention, wherein said method is characterized in that a bis(alkoxymethylphenol), being a bisphenol expressed by the aforementioned General Formula (3) where R is an *aliphatic hydrocarbon group that may have an* aromatic hydrocarbon group, hydroxyl group or [aliphatic hydrocarbon group that may have an] ether group, is obtained by causing a bisphenol expressed by the aforementioned General Formula (5) to react with formaldehyde in the presence of an alkali catalyst and then causing the obtained bis(hydroxymethylphenol) expressed by the aforementioned General Formula (6) to further react with an alcohol expressed by General Formula (7) specified below in the presence of an acid catalyst, is a favorable embodiment of the present invention.

[Chemical 7]

R—OH General Formula (7)

(In the formula, R represents an *aliphatic hydrocarbon group that may have an* aromatic hydrocarbon group, hydroxyl group or [aliphatic hydrocarbon group that may have an] ether group.)

Also, a method for producing a polynuclear poly (formylphenol), wherein with respect to a polynuclear polyphenol expressed by the aforementioned General Formula (1), the polynuclear polyphenol where m in the formula is an integer of 0, 1 or 2, but where if m is 0, then X is a trivalent to hexavalent bond group with l+n being 3 to 6, is a polynuclear polyphenol expressed by General Formula (8) specified below, and wherein similarly the polynuclear poly (formylphenol) expressed by the aforementioned General Formula (2) is a polynuclear poly(formylphenol) expressed by General Formula (9) specified below, is another favorable embodiment of the present invention.

General Formula (8)

[Chemical 8]

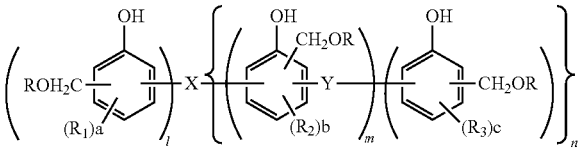

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an]ether group. $R_1$, $R_2$ and $R_3$ may be the same or different and respectively represent a hydrocarbon group, hydrocarbon group containing oxygen atom, hydroxyl group, halogen group or halogenated hydrocarbon group; a and c respectively indicate an integer of 0 or 1 to 3, while b indicates an integer of 0, 1 or 2; l and n respectively indicate an integer of 1 to 3; m indicates an integer of 0, 1 or 2; X indicates a bond group or a single bond; and Y indicates a bivalent alkylene group. If m is 0, however, X is a trivalent to hexavalent bond group and l+n is 3 to 6.)

General Formula (9)

[Chemical 9]

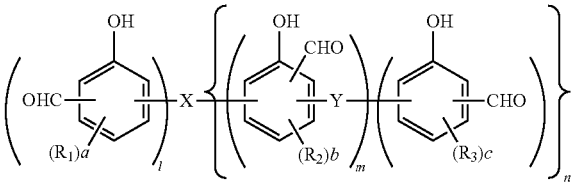

(In the formula, $R_1$, $R_2$, $R_3$, a, b, c, l, m, n, X and Y indicate the same things represented by the corresponding symbols in General Formula (8).)

Also, a method for producing a polynuclear poly (formylphenol)according to an embodiment of the present invention, wherein said method is characterized in that a polynuclear poly(hydroxymethylphenol) expressed by General Formula (11) specified below, being a polynuclear polyphenol expressed by the aforementioned General Formula (8) where R is a hydrogen atom, is obtained by causing a polynuclear polyphenol expressed by General Formula (10) specified below to react with formaldehyde in the presence of an alkali catalyst, is a favorable embodiment of the present invention.

General Formula (10)

[Chemical 10]

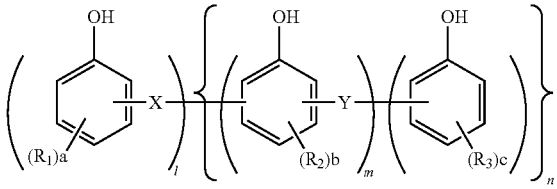

(In the formula, $R_1$, $R_2$, $R_3$, a, b, c, l, m, n, X and Y indicate the same things represented by the corresponding symbols in General Formula (1), and at least one of the o-position and p-position of the hydroxyl group is not substituted. If m is 0, however, X is a trivalent to hexavalent bond group and l+n is 3 to 6.)

General Formula (11)

[Chemical 11]

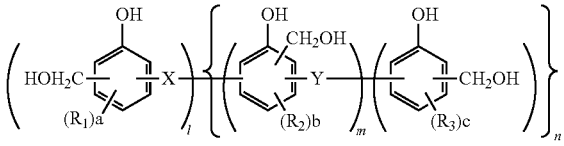

(In the formula, $R_1$, $R_2$, $R_3$, a, b, c, l, m, n, X, and Y indicate the same things represented by the corresponding symbols in General Formula (1), and the substitution position of the hydroxy methyl group corresponds to the o-position or p-position relative to the hydroxyl group. If m is 0, however, X is a trivalent to hexavalent bond group and l+n is 3 to 6.)

Also, a method for producing a polynuclear poly (formylphenol)according to an embodiment of the present invention, wherein said method is characterized in that a polynuclear poly(alkoxymethylphenol), being a polynuclear polyphenol expressed by the aforementioned General Formula (8) where R is an *aliphatic hydrocarbon group that may have an* aromatic hydrocarbon group, hydroxyl group or [aliphatic hydrocarbon group that may have an] ether group, is obtained by causing a polynuclear polyphenol expressed by the aforementioned General Formula (10) to react with formaldehyde in the presence of an alkali catalyst and then causing the obtained polynuclear poly(hydroxymethylphenol) expressed by the aforementioned General Formula (11) to further react with an alcohol expressed by General Formula (12) specified below in the presence of an acid catalyst, is a favorable embodiment of the present invention.

[Chemical 12]

R—OH General Formula (12)

(In the formula, R represents an *aliphatic hydrocarbon group that may have an* aromatic hydrocarbon group, hydroxyl group or [aliphatic hydrocarbon group that may have an] ether group.)

Under a production method conforming to the present invention, the target compound, or polynuclear poly (formylphenol), is expressed by the aforementioned General Formula (2), where $R_1$, $R_2$ and $R_3$ may be the same or different and respectively represent a hydrocarbon group, hydrocarbon group containing oxygen atom, hydroxyl group, halogen group or halogenated hydrocarbon group, but preferably a hydrocarbon group. Bond group X is a single bond or bivalent to hexavalent bond group, such as a hydrocarbon group, oxygen atom-containing group, sulfur atom-containing group, nitrogen atom-containing group or halogen atom-containing group, but preferably a hydrocarbon group. Bond group Y is a bivalent alkylene group.

Also, a and c (indicated by n in General Formulas (3) to (6)) respectively indicate an integer of 0 or 1 to 3; b indicates an integer of 0, 1 or 2; l and n respectively indicate an integer of 1 to 3; and m indicates an integer of 0, 1 or 2. Here, if m is 0 and X is a bivalent bond group or a single bond and l+n is 2, then the polynuclear poly(formylphenol) is a bis(formylphenol). If m is not 0, or X is a trivalent to hexavalent bond group and l+n is 3 to 6, then the polynuclear poly(formylphenol) is a polynuclear poly(formylphenol) having three or more hydroxy-substituted phenol nuclei in its skeletal structure.

Accordingly, under a production method conforming to the present invention, the target compound, or polynuclear poly (formylphenol) expressed by the aforementioned General Formula (2), is represented by a bis(formylphenol) expressed by the aforementioned General Formula (4) if, in the formula, m is 0, X is a bivalent bond group or a single bond and l+n is 2. Here, in the aforementioned General Formula (4), X is a bivalent bond group or a single bond, where the bivalent bond group, although not specifically limited as long as it is a bis(formylphenol) having a bond group to which a production method under the present invention can be applied, may be a hydrocarbon group, oxygen atom-containing group, sulfur atom-containing group, nitrogen atom-containing group or halogen atom-containing group, among others. Examples of the hydrocarbon group include a saturated or unsaturated hydrocarbon group, polycyclic or monocyclic alicyclic hydrocarbon group, aromatic hydrocarbon group or heterocyclic hydrocarbon group, of straight or branched chain that may have a substitution group.

As for the aforementioned bivalent hydrocarbon group, specific examples include, among others: bivalent noncyclic saturated hydrocarbon groups with a carbon atom number of 1 to 30, or preferably 1 to 15, such as methylene, ethylene, propylene, 2,2-propylidene, 1,1-propylidene, 2,2-butylidene, hexamethylene, n-dodecylene and other alkylene groups and alkylidene groups; bivalent noncyclic unsaturated hydrocarbon groups such as vinylene, 1,2-ethinediyl, propenylene, 2,4-hexadiene-1,6-ylene, 2-butenylene and 2-methylene-1,3-propandiyl; bivalent monocyclic alicyclic hydrocarbon groups with a carbon atom number of 3 to 15, or preferably 5 to 10, such as cyclopentylidene, cyclohexylidene, 1,4-cyclohexylene, 1,2-cyclohexenylene and 2,4-cyclohexadiene-1-ylidene; bivalent monocyclic aromatic hydrocarbon groups such as P-phenylene, 2-propyl-1,4-phenylene and other phenylene groups; bivalent condensed polycyclic hydrocarbon groups such as 2,3-indenylidene, 1,2-naphthylene, 2,7-phenanthrene and 9,9-fluorenylidene; bivalent crosslinked cyclic hydrocarbon groups such as bicyclo[2.2.1]heptane-2,3-diyl, 6-ethyl bicyclo[2.2.1]heptane-2,3-diyl, tetracyclo[$4.4.0.1^{2,5}0.1^{7,10}$]dodecene-3,4-diyl and adamantane-1,3-diyl; bivalent spiro hydrocarbon groups such as spiro[3.4]octane-7,8-diyl; bivalent polycyclic aggregated hydrocarbon groups such as 1,1'-biphenyl-4,4'-diyl, p-terphenyl-4,4"-diyl, 1,1'-diphenyl methane-4,4'-diyl and stilbene-4,4'-diyl; and terpene hydrocarbon groups such as 2-pinene-10-ylidene and 5-norbornene-2,3-diyl.

Substitution groups that can be contained in the aforementioned bivalent hydrocarbon groups include bivalent substitution groups or monovalent substitution groups that can act as a bond group, where specific examples include, among others, the aforementioned bivalent hydrocarbon groups or monovalent hydrocarbon groups corresponding to the aforementioned bivalent hydrocarbon groups, such as monovalent noncyclic saturated hydrocarbon groups, noncyclic unsaturated hydrocarbon groups, monocyclic alicyclic hydrocarbon groups, monocyclic aromatic hydrocarbon groups, condensed polycyclic hydrocarbon groups, crosslinked cyclic hydrocarbon groups, polycyclic aggregated hydrocarbon groups, spiro hydrocarbon groups and terpene hydrocarbon groups. To be specific, examples include, among others: monovalent noncyclic saturated hydrocarbon groups with a carbon atom number of 1 to 30, or preferably 1 to 15, such as methyl, ethyl, isopropyl, tert-butyl, sec-butyl, isobutyl, t-octyl, n-dodecyl and other alkyl groups; monovalent noncyclic unsaturated hydrocarbon groups such as vinyl, aryl, hexa-2,4-diene-1-yl and butane-2-en-1-yl; monovalent monocyclic alicyclic hydrocarbon groups with a carbon atom number of 3 to 15, or preferably 5 to 10, such as cyclopentyl, cyclohexyl, cyclohexene-1-yl and cyclohexa-2,5-diene-1-yl; monovalent monocyclic aromatic hydrocarbon groups such as phenyl, 2-propyl-phenyl and other phenyl groups; monovalent condensed polycyclic hydrocarbon groups such as indene-2-yl, 1-naphthyl, phenanthrene-2-yl and fluorene-9-yl; monovalent crosslinked cyclic hydrocarbon groups such as bicyclo[2.2.1]heptane-2-yl, 6-ethyl bicyclo[2.2.1]heptane-2-yl, tetracyclo[$4.4.0.1^{2.5}0.1^{7,10}$]dodecene-3-yl and adamantane-2-yl; monovalent spiro hydrocarbon groups such as spiro[3.4]octane-7-yl; monovalent polycyclic aggregated hydrocarbon groups such as 1,1'-biphenyl-4-yl, P-terphenyl-4-yl, 1,1'-diphenyl methane-4-yl and stilbene-4-yl; and terpene hydrocarbon groups such as 2-pinene-10-yl and 5-norbornene-2-yl.

Hydrocarbon groups containing the aforementioned substitution groups include, among others, methyl ethyl methylene, methyl isobutyl methylene, cyclohexyl methyl methylene, dicyclohexyl methylene, diphenyl methylene, phenyl methylene and biphenyl methylene. Also, examples of substitution groups containing at least one of an oxygen atom, nitrogen atom, sulfur atom and halogen atom, etc., include: substitution groups containing monovalent methoxy, ethoxy, cyclohexyloxy or other alkoxy group, phenoxy or other aryloxy group, 4-methoxy phenyl group, 2-methoxy phenyl group, furyl group or other ether group; substitution groups containing a carbonyl group such as an acetyl, propionyl, butyryl benzoyl or other acyl group; substitution groups containing a primary, secondary or tertiary ester group such as an acryloyloxy, methacryloyloxy, acetoxy, t-butoxy, benzoyloxy or other acyloxy group; substitution groups containing an hydroxyl group such as a hydroxyl group or 4-hydroxy phenyl, 4-hydroxy phenol methyl, 3-hydroxy-n-butyl or 2-hydroxy ethyloxy; and fluorine atoms and other halogen atoms, halogenated hydrocarbon groups, monovalent amino groups, bivalent ether groups, carbonyl groups, ester groups, amid groups, imino groups, sulfide groups, and the like.

Accordingly, specific examples of bivalent hydrocarbon groups containing a substitution group including at least one of an oxygen atom, nitrogen atom, sulfur atom and halogen atom include, among others: di(trifluoromethyl)methylene group, 4-hydroxy-3-methoxy phenyl methylene group (Chemical Formula 1) and other substituted methylene groups. Other examples include a group expressed by Chemical Formula 2 specified below where two methylene groups are provided at both ends of a hydroxy phenylene group, as well as other monovalent heterocyclic groups such as thiophene-2-yl, furan-2-yl, quinoline-2-yl, 2H-pyran-2-yl and 1,4-dihydro-4-pyridyl.

Chemical Formula 1

[Chemical 13]

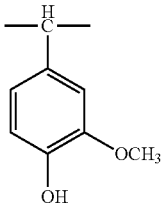

Chemical Formula 2

[Chemical 14]

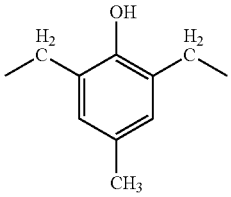

Furthermore, specific examples of bivalent bond groups where bond group X is an oxygen atom-containing group, sulfur atom-containing group, nitrogen atom-containing group or halogen atom-containing group include, among others: bivalent hetero compound groups such as a carbonyl group, ether group, oxocarbonyl group (carboxylate group), sulfide group, sulfoxide group, sulfone group, thioketone group, thiocarbonyl group, carbonyl dioxy group, sulfonyl dioxy group, azo group, hydrazo group, imino group and ureilene group; or bond groups that bond a hydroxy phenyl group in General Formula (3) or (4) specified below via any of the foregoing with a hydrocarbon group, such as 1,1'-diphenyl ether-4,4'dicarbonyl group, 1,1'-diphenyl sulfide-4,4'-dicarbonyl group, terephthaloyl group, 4,4'-methylene dioxy diphenyl group, 2,6-naphthylene dioxy group, methylene dioxy group, malonyl group, succinyl group, fumaloyl group and maloyl group. Favorable choices as the overall bond group X include saturated hydrocarbon groups, hydrocarbon groups containing an unsaturated bond including only aromatic hydrocarbon groups, saturated hydrocarbon groups containing a primary or secondary ester group, and saturated hydrocarbon groups containing an ether group (excluding 1,2-epoxide, 1,3-epoxide and acetal groups), among which saturated hydrocarbon groups, and hydrocarbon groups containing an unsaturated bond including only aromatic hydrocarbon groups, are particularly desirable.

General Formula (3)

[Chemical 15]

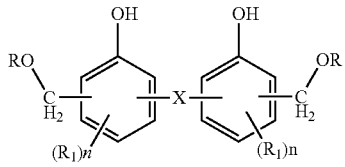

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an] ether group, where n indicates an integer of 0 or 1 to 3. Both $R_1$s may be the same or different and respectively represent a hydrocarbon group, hydrocarbon group containing oxygen atom, halogenated hydrocarbon group, hydroxyl group or halogen group. X indicates a bivalent bond group or a single bond.)

General Formula (4)

[Chemical 16]

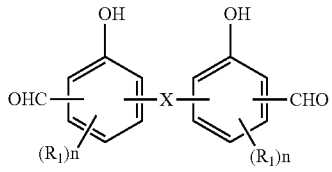

(In the formula, $R_1$, n and X indicate the same things represented by the corresponding symbols in General Formula (3).)

Also, with respect to a bis(formylphenol) expressed by General Formula (4), $R_1$ in the formula represents a hydrocarbon group, hydrocarbon group containing oxygen atom, halogenated hydrocarbon group, hydroxyl group or halogen group, where n indicates an integer of 0 or 1 to 3, and if n is 2 or 3, both $R_1$s may be the same or different.

As for $R_1$, if $R_1$ is a hydrocarbon group, then it is a monovalent hydrocarbon group that can be substituted to the aforementioned bond group X, where specific examples of such hydrocarbon group include, among others, a saturated or unsaturated hydrocarbon group, polycyclic or monocyclic alicyclic hydrocarbon group, aromatic hydrocarbon group or heterocyclic hydrocarbon group, of straight or branched chain which may have a substitution group.

Specific examples of the aforementioned monovalent hydrocarbon group include, among others: monovalent noncyclic saturated hydrocarbon groups with a carbon atom number of 1 to 30, or preferably 1 to 15, such as methyl, ethyl, isopropyl, tert-butyl, sec-butyl, isobutyl, n-hexyl, t-octyl, n-dodecyl and other alkyl groups; monovalent noncyclic unsaturated hydrocarbon groups such as vinyl, aryl, hexa-2, 4-diene-1-yl and 2-butane-1-yl; monovalent monocyclic alicyclic hydrocarbon groups with a carbon atom number of 3 to 15, or preferably 5 to 10, such as cyclopentyl, cyclohexyl, 4-n-butyl cyclohexyl, 2-cyclohexe-3-yl and cyclohexa-2,5-diene-1-yl; monovalent monocyclic aromatic hydrocarbon groups such as phenyl and 2-propyl-phenyl; monovalent condensed polycyclic hydrocarbon groups such as indene-2-yl, 1-naphthyl, phenanthrene-2-yl and fluorene-9-yl; monovalent crosslinked cyclic hydrocarbon groups such as bicyclo[2.2.1]heptane-2-yl, 6-ethyl bicyclo[2.2.1]heptane-2-yl, tetracyclo[4.4.0.1$^{2,5}$0.1$^{7,10}$]dodecene-3-yl and adamantane-2-yl; monovalent spiro hydrocarbon groups such as spiro[3.4]octane-7-yl; monovalent polycyclic aggregated hydrocarbon groups such as 1,1'-biphenyl-4-yl, P-terphenyl-4-yl, 1,1'-diphenyl methane-4-yl and stilbene-4-yl; terpene hydrocarbon groups such as 2-pinene-10-yl and 5-norbornene-2-yl; and monovalent heterocyclic hydrocarbon groups such as furan-2-yl and 2H-pyran-2-yl. Substitution groups that can be substituted to these monovalent hydrocarbon groups are the same as the monovalent hydrocarbon groups that can be substituted to bivalent hydrocarbon groups pertaining to bond group X.

The oxygen atom-containing hydrocarbon group is a hydrocarbon group where one or more oxygen atoms bond in the chemical structure, where specific examples include, among others: substitution groups containing a methoxy, ethoxy, cyclohexyloxy or other alkoxy group, phenoxy or other aryloxy group, 4-methoxy phenyl group, 2-methoxy phenyl group, furyl group or other ether group; substitution groups containing a carbonyl group such as an acetyl, propionyl, butyryl benzoyl or other acyl group; substitution groups containing a primary, secondary or tertiary ester group such as an acryloyloxy, methacryloyloxy, t-butoxy, acetoxy, benzoyloxy or other acyloxy group; and substitution groups containing an hydroxyl group such as 4-hydroxy phenyl, 4-hydroxy phenol methyl, 3-hydroxy-n-butyl or 2-hydroxy ethyloxy.

Examples of halogenated hydrocarbon groups include trifluoromethyl and 3-bromo-n-propyl.

If $R_1$ is a halogen group, then specific examples include a chlorine atom, bromine atom and fluorine atom, among others.

Favorable forms of $R_1$ are those having a carbon atom number of 1 to 20, and oxygen atom number of 0 to 2, where an alkyl group with a carbon atom number of 1 to 10 and cycloalkyl group with a carbon atom number of 5 to 10 are particularly desirable. Cases where $R_1$ is a hydrocarbon having a hydroxyl group, ether group or halogen group (bromine, chlorine, etc.,) in the α-position, or specifically a hydroxy methyl group or alkoxy methyl group having such characteristics, are not desirable. Take note, however, that if n is 2 or 3, then all substitution positions of $R_1$ may be the same or different.

As for a bis(formylphenol) expressed by General Formula (4), the substitution position of the formyl group should desirably be the ortho position or para position relative to the hydroxyl group. For example, a compound expressed by General Formula (13) or (14) specified below is desirable.

General Formula (13)

[Chemical 17]

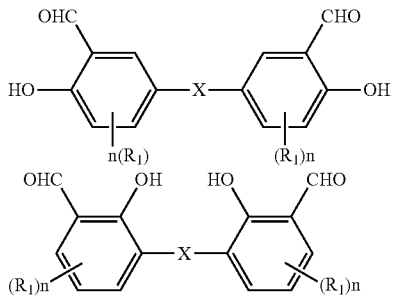

(In the formula, $R_1$, n and X indicate the same things represented by the corresponding symbols in General Formula (3).)

General Formula (14)

[Chemical 18]

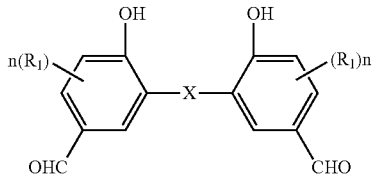

(In the formula, $R_1$, n and X indicate the same things represented by the corresponding symbols in General Formula (3).)

Accordingly, specific compounds corresponding to a bis(formylphenol) expressed by the aforementioned General Formula (4) include the following, for example:

4,4'-methylene bis(2-methyl-4-formylphenol),
2,2'-methylene bis(4-methyl-6-formylphenol),
4,4'-methylene bis(2-bromo-6-formylphenol),
2,2-bis(3-formyl-4-hydroxy phenyl)propane,
1,2-bis(3-formyl-4-hydroxy-5-methoxy phenyl)ethane,
3,3'-dimethyl-5,5'-diformyl-4,4'-biphenol,
1,3-bis(3-formyl-4-hydroxyphenyl)adamantane, and
1,3-bis(3-formyl-5-methyl-4-hydroxyphenyl)adamantane Compound 1

[Chemical 19]

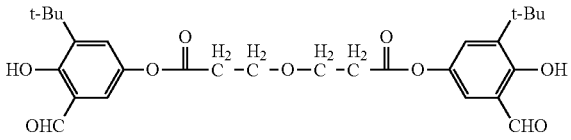

Compound 2

[Chemical 20]

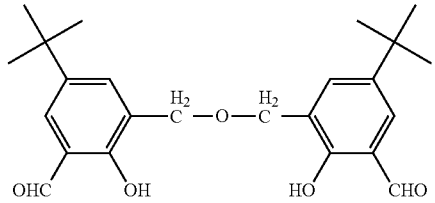

Under a production method conforming to the present invention, the target substance corresponding to the material, or a bis(formylphenol) expressed by General Formula (4), can be produced by causing a bisphenol expressed by General Formula (3) to react with hexamethylene tetramine in the presence of an acid and then hydrolyzing the obtained reaction product.

General Formula (3)

[Chemical 21]

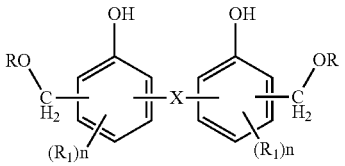

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an] ether group, where n indicates an integer of 0 or 1 to 3. Both $R_1$s may be the same or different and respectively represent a hydrocarbon group, hydrocarbon group containing oxygen atom, halogenated hydrocarbon, hydroxyl group or halogen group. X indicates a bivalent bond group or a single bond.)

Under a production method conforming to the present invention, the bisphenol expressed by the aforementioned General Formula (3) representing the direct material compound may be such that in the formula, R may be a hydrogen atom or *an aliphatic hydrocarbon group that may have an* aromatic hydrocarbon group, hydroxyl group, or [aliphatic hydrocarbon group that may have an] ether group, and X, $R_1$ and n indicate the same things represented by the corresponding symbols in General Formula (4). Accordingly, specifically X, $R_1$ and n may be the same as or different from X, $R_1$ and n in the aforementioned General Formula (4), and for example, the substitution group of X or $R_1$ may be hydrolyzed as long as the bisphenol skeletal can be maintained. However, it is desirable that X and $R_1$ remain stable, or unchanged, during the course of reaction.

Similarly with the bisphenol expressed by General Formula (3), a compound where the substitution position of the hydroxy methyl group or alkoxy methyl group is the ortho position or para position relative to the hydroxyl group is desired.

On the other hand, R is a hydrogen atom or *an aliphatic hydrocarbon group that may have an* aromatic hydrocarbon group, hydroxyl group, or [aliphatic hydrocarbon group that may have an] ether group, where the *aliphatic hydrocarbon group that may have an* aromatic hydrocarbon group, hydroxyl group, or [aliphatic hydrocarbon group that may have an] ether group, should desirably be a substituted or unsubstituted saturated aliphatic hydrocarbon group such as an alkyl group, alkoxy alkyl group or phenyl alkyl group, etc., where a primary or secondary substituted or unsubstituted alkyl group is desirable. This alkyl group may be an alkyl group with a carbon atom number of 1 to 20, or desirably a methyl group, isopropyl group, n-butyl group or other alkyl group of straight or branched chain with a carbon atom number of 1 to 10 or cycloalkyl group with a carbon atom number of 5 to 10.

As for bond group X, one having both hydroxy phenyl groups bonded on the same carbon of bond group X is desirable, where specific examples include compounds expressed by General Formulas (15) and (16) specified below, among others. When a bisphenol having such chemical structure is used as the material, the yield will increase compared to when the Duff reaction is used, which is desirable.

General Formula (15)

[Chemical 22]

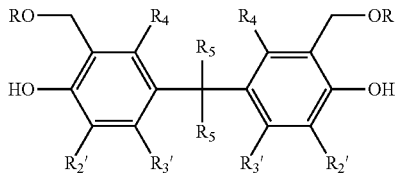

General Formula (16)

[Chemical 23]

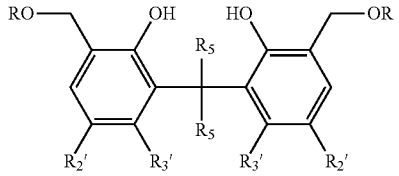

In the above formulas, R is the same as in General Formula (3), where $R_2'$, $R_3'$ and $R_4$ are independent of each other and a hydrogen atom or the same as $R_1$ in General Formula (3), while $R_5$ and $R_6$ are the same as a monovalent hydrocarbon group that can be substituted to a bivalent hydrocarbon group of bond group X, or a hydrogen atom.

Favorable forms of $R_5$ and $R_6$ are independent hydrogen atoms or alkyl groups with a carbon atom number of 1 to 10, cycloalkyl groups with a carbon atom number of 5 to 10, or alicyclic or crosslinked alkylidene group with a carbon atom number of 5 to 20 forming a ring containing the carbon atoms of the bond group.

In the aforementioned General Formulas (15) and (16), it is desirable that $R_2'$ have a substitution group, not hydrogen atom, for such reasons as inexpensive material, high yield, ease of obtaining highly pure substance via crystallization, etc.

In General Formula (16), it is desirable that at least one of $R_5$ and $R_6$ be a hydrogen atom, because then in many cases a bisphenol being the material corresponding to a compound expressed by General Formula (16) can be obtained relatively easily by causing $R_2'$ to react with an alkyl group-containing p-alkyl phenol and aldehyde in the presence of an acid catalyst.

In General Formula (15), it is desirable that $R_5$ and $R_6$ be both hydrogen atoms and $R_2'$ be an alkyl group, because then a bis(hydroxymethylphenol) expressed by General Formula (15), being the direct material under the present invention and where R is hydrogen, can be obtained by causing a O-alkyl phenol being the material phenol to react with formaldehyde in the presence of an alkali catalyst, without removing 4,4'-methylene bisphenol from the reactor.

This reaction formula is specified below.

Reaction Formula 1

[Chemical 24]

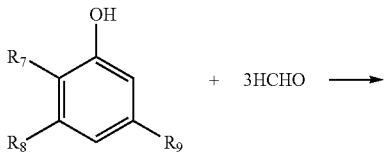

-continued

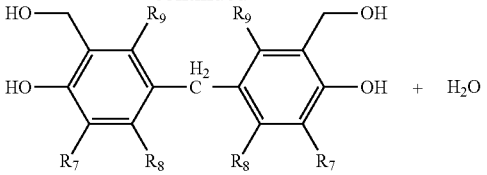

(In the formula, $R_7$ represents an alkyl group, while $R_8$ and $R_9$ respectively represent a hydrogen atom or alkyl group.)

Specific compounds corresponding to a bisphenol expressed by General Formula (3), which is the material compound used in a production method conforming to the present invention, include the following, for example:

4,4'-methylene bis(2-methyl-6-hydroxymethylphenol),
4,4'-methylene bis(2-hydroxy methyl phenol),
4,4'-methylene bis(2,5-dimethyl-6-hydroxymethylphenol),
4,4'-methylene bis(2-methoxy-6-hydroxymethylphenol),
2,2'-methylene bis(4-methyl-6-hydroxymethylphenol),
2,2'-bis(3-methyl-4-hydroxy-5-hydroxymethylphenyl)propane,
2,2'-bis(3-hydroxy methyl-4-hydroxyphenyl)propane,
9,9-bis(3-phenyl-4-hydroxy-5-hydroxymethylphenyl)fluorenone,
2,6-bis {(2-hydroxy-3-hydroxymethyl-5-methylphenyl)methyl}-4-methylphenol,
2,6-bis {(2,5-dimethyl-3-hydroxymethyl-4-hydroxyphenyl) methyl}-4-methylphenol,
2,6-bis {(3-methyl-4-hydroxy-5-hydroxymethylphenyl)methyl}-4-methylphenol,
2,4-bis {(2,5-dimethyl-3-hydroxymethyl-4-hydroxy phenyl) methyl}-3,6-dimethylphenol,
Bis[3-(3-methyl-4-hydroxy-5-hydroxymethylphenyl)methyl-2,5-dimethyl-4-hydroxyphen yl]methane,
3,3'-dimethyl-5,5'-di(hydroxymethyl)-4,4'-biphenol,
1,3-bis(3-methyl-4-hydroxy-5-hydroxymethylphenyl)adamantane,
1,4-bis{1-(3-methyl-4-hydroxy-5-hydroxymethylphenyl) isopropyl}benzene,
3,4-bis(3-hydroxy methyl-4-hydroxyphenyl)-3-hexene, and
3,4-bis(3-hydroxy methyl-4-hydroxyphenyl)hexane Also, under a production method conforming to the present invention, the target compound, or a polynuclear poly (formylphenol) expressed by the aforementioned General Formula (2), is a polynuclear poly(formylphenol) expressed by the aforementioned General Formula (8) and having three or more hydroxy-substituted phenyl nuclei when, in the formula, m is an integer of 0, 1 or 2, but when m is 0, X is a trivalent to hexavalent bond group and l+n is 3 to 6. Here, in the aforementioned General Formula (8), X is a single bond or bivalent to hexavalent bond group, but when m is 0, X is a trivalent to hexavalent bond group. X should desirably be a bivalent to tetravalent bond group. Such bivalent to hexavalent bond group is not specifically limited, as long as it is a polynuclear poly(formylphenol) to which a production method under the present invention can be applied. However, it may be a hydrocarbon group, oxygen atom-containing group, sulfur atom-containing group, nitrogen atom-containing group, halogen atom-containing group, etc. Desired examples of the bivalent to hexavalent hydrocarbon group that may have a substitution group include a saturated or unsaturated hydrocarbon group, polycyclic or monocyclic alicylcic hydrocarbon group or aromatic hydrocarbon group of direct or branched chain with a carbon atom number of 1 to 30; condensed polycyclic hydrocarbon group such as 9,9-fluorenylidene; crosslinked cyclic hydrocarbon group such as adamantane-2,3-diyl; spiro hydrocarbon group such as spiro [3.4]octa-7,8-diyl; polycyclic aggregated hydrocarbon group such as P-terphenyl-4,4"-diyl; terpene hydrocarbon group such as 5-norbornene-2,3-diyl; and heterocyclic hydrocarbon group such as 2,5-thiophendiyl.

The aforementioned bivalent to hexavalent hydrocarbon groups may have bivalent substitution groups or monovalent substitution groups that can act as a bond group.

Among the above, favorable choices for X include, for example, trivalent saturated or unsaturated hydrocarbon groups expressed by the chemical formulas specified below, methine group (Chemical Formula 3), ethylidyne group (Chemical Formula 4), cyclohexane-1,1,4-tolyl group (Chemical Formula 5), propylidine group (Chemical Formula 6), propane-1,2,3-tolyl group, butane-1,3,3-tolyl group (Chemical Formula 7), and 1,4,4-cyclohexane-1-en-tolyl group (Chemical Formula 8).

[Chemical 25]

Chemical Formula 3

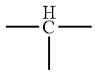

Chemical Formula 4

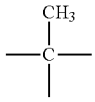

Chemical Formula 5

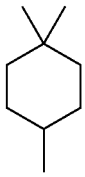

Chemical Formula 6

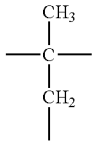

Chemical Formula 7

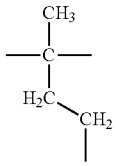

Chemical Formula 8

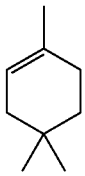

Examples include tetravalent saturated or unsaturated hydrocarbon groups expressed by the chemical formulas specified below, ethane-1,1,2,2-tetrayl group (Chemical Formula 9), 1,1,4,4-cyclohexane-tetrayl group (Chemical Formula 10), methane tetrayl group (Chemical Formula 11), ethylene diylidene group (Chemical Formula 12), and 1,1,4,4-cyclohexane-2-en-tetrayl group (Chemical Formula 13).

[Chemical 26]

Chemical Formula 9

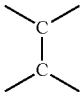

Chemical Formula 10

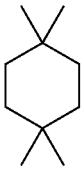

Chemical Formula 11

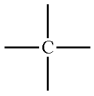

Chemical Formula 12

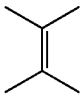

Chemical Formula 13

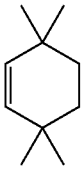

For example, aromatic hydrocarbon groups, etc., expressed by the chemical formula specified below can be considered.

(Chemical Formula 14)

[Chemical 27]

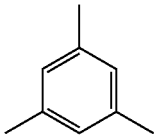

Benzene triyl group

Furthermore, specific examples of bivalent to hexavalent bond groups when bond group X is an oxygen atom-containing group, sulfur atom-containing group, nitrogen atom-containing group or halogen atom-containing group include, among others, bivalent to hexavalent chain or cyclic compound groups having a hetero atom, such as a ketone group, ether group, oxocarbonyl group (carboxylate group), sulfide group, sulfoxide group, sulfone group, thioketone group, thiocarbonyl group, carbonyl dioxy group, sulfonyl dioxy group, azo group, hydrazo group, imino group, ureilene group or hydrocarbon group having halogen atom.

Also, Y indicates a bivalent alkylene group, or desirably a saturated hydrocarbon group of straight or branched chain with a carbon atom number of 1 to 5.

Also, with respect to a polynuclear poly(formylphenol) expressed by General Formula (9), $R_1$, $R_2$ and $R_3$ in the formula may be the same or different, and respectively represent a hydrocarbon group, hydrocarbon group containing oxygen atom, hydroxyl group, halogen group or halogenated hydrocarbon group, while a and c respectively indicate an integer of 0 or 1 to 3, and b indicates an integer of 0, 1 or 2.

Examples of such hydrocarbon group include a monovalent saturated or unsaturated hydrocarbon group, polycyclic or monocyclic alicylcic hydrocarbon group or aromatic hydrocarbon group of direct or branched chain that may have a substitution group.

Specific examples of the aforementioned monovalent hydrocarbon group include, among others: monovalent noncyclic saturated hydrocarbon groups with a carbon atom number of 1 to 30, or preferably 1 to 15, such as methyl, ethyl, isopropyl, t-butyl, sec-butyl, isobutyl, t-octyl, n-dodecyl and other alkyl groups; monovalent noncyclic unsaturated hydrocarbon groups such as vinyl, aryl, hexa-2,4-diene-1-yl and buta-2-en-1-yl; monovalent monocyclic alicyclic hydrocarbon groups with a carbon atom number of 3 to 15, or preferably 5 to 7, such as cyclopentyl, cyclohexyl, 2-cyclohexe-3-yl and cyclohexa-2,5-diene-1-yl; monovalent monocyclic aromatic hydrocarbon groups such as phenyl and 2-propyl-phenyl; polycyclic aromatic hydrocarbon groups such as 1-naphthyl, phenanthrene-2-yl; monovalent condensed polycyclic hydrocarbon groups such as indene-2-yl and fluorene-9-yl; monovalent crosslinked cyclic hydrocarbon groups such as bicyclo[2.2.1]hepto-2-yl, 6-ethyl bicyclo[2.2.1]hepto-2-yl, tetracyclo[4.4.0.$1^{2,5}$.$1^{7,10}$]dodecene-3-yl and adamantane-2-yl; monovalent spiro hydrocarbon groups such as spiro[3.4]octa-7-yl; monovalent polycyclic aggregated hydrocarbon groups such as 1,1'-biphenyl-4-yl, P-terphenyl-4-yl, 1,1'-diphenyl methane-4-yl and stilbene-4-yl; terpene hydrocarbon groups such as 2-pinene-10-yl and 5-norbornene-2-yl; and monovalent heterocyclic hydrocarbon groups such as furan-2-yl and 2H-pyran-2-yl.

The oxygen atom-containing hydrocarbon group is a hydrocarbon group where one or more oxygen atoms bond in the chemical structure, where specific examples include, among others: substitution groups containing a methoxy, ethoxy, cyclohexyloxy or other alkoxy group, phenoxy or other aryloxy group, 4-methoxy phenyl group, 2-methoxy phenyl group, furyl group or other ether group; substitution groups containing a carbonyl group such as an acetyl, propionyl, butyryl benzoyl or other acyl group; substitution groups containing a primary, secondary or tertiary ester group such as an acryloyloxy, methacryloyloxy, acetoxy, benzoyloxy or other acyloxy group; substitution groups containing an hydroxyl group such as 4-hydroxy phenyl, 4-hydroxy phenol methyl, 3-hydroxy-n-butyl or 2-hydroxy ethyloxy; and monovalent heterocyclic hydrocarbon groups such as furan-2-yl and 2H-pyran-2-yl.

Specific examples of the halogen group include, among others, a chlorine atom, bromine atom and fluorine atom. The halogenated hydrocarbon group may be a halogenated alkyl group such as a trifluoromethyl group.

Favorable forms of $R_1$, $R_2$ and $R_3$ are those having a carbon atom number of 1 to 20 and an oxygen atom number of 0 to 2, and especially an alkyl group with a carbon atom number of 1 to 10 or cycloalkyl group with a carbon atom number of 5 to 10 is desirable.

Also, the substitution positions of $R_1$, $R_2$ and $R_3$ may be the same or different when a and c are 2 or 3, orb is 2.

Furthermore, l and n respectively indicate an integer of 1 to 3, while m indicates an integer of 0, 1 or 2. If m is 0, however, l+n is 3 to 6. A desired combination of l, n and m is such that m is 0 and l+n is 3 or 4, or m is 1 and l and n are both 1. Also, substitution groups $R_1$ and $R_3$ should desirably be the same and their substitution positions relative to the OH group should also be the same. If m is 0, the OH group should desirably be in position 4 relative to the bond position of bond group X in the phenyl nucleus. If m is not 0, the OH group should desirably be in position 2 relative to the bond positions of bond groups X and Y in the phenyl nucleus.

Also, with respect to a polynuclear poly(formylphenol) expressed by General Formula (9), it is desirable that the substitution position of the formyl group be the ortho position or para position relative to the hydroxyl group.

Examples include compounds expressed by General Formulas (17), (18) and (19) specified below.

General Formula (17)

[Chemical 28]

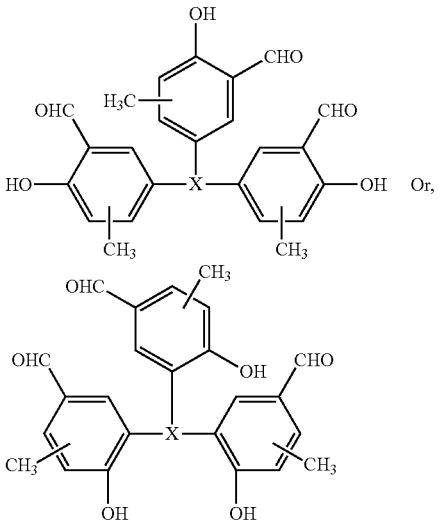

(In the formula, X is a trivalent bond group, $R_1$ and $R_3$ are methyl groups, a and c are both 1, m is 0, and l+n is 3, according to General Formula (9).)

General Formula (18)

[Chemical 29]

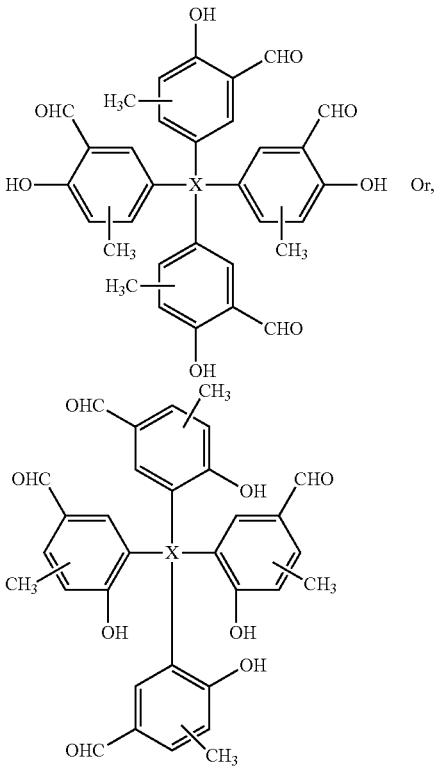

(In the formula, X is a tetravalent bond group, $R_1$ and $R_3$ are methyl groups, a and c are both 1, m is 0, and l+n is 4, according to General Formula (9).)

General Formula (19)

[Chemical 30]

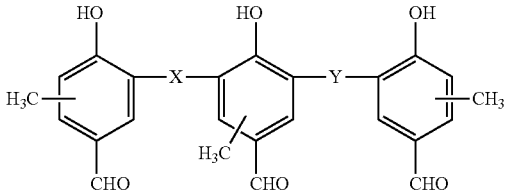

(In the formula, X is a bivalent bond group, $R_1$, $R_2$ and $R_3$ are methyl groups, a, b and c are 1, m is 0, and l+n is 1, according to General Formula (9).)

Accordingly, specific compounds conforming to a polynuclear poly(formylphenol) expressed by General Formula (9) include, for example, 1-[α-methyl-α-(3-formyl-5-methyl-4-hydroxyphenyl)ethyl]-4-[α,α-bis(3-formyl-5-methy 1-4-hydroxyphenyl)ethyl]benzene.

Under a production method conforming to the present invention, the target substance corresponding to the material, or a polynuclear poly(formylphenol) expressed by General Formula (9), can be produced by causing a polynuclear polyphenol expressed by General Formula (8) to react with hexamethylene tetramine in the presence of an acid and then hydrolyzing the obtained reaction product.

General Formula (8)

[Chemical 31]

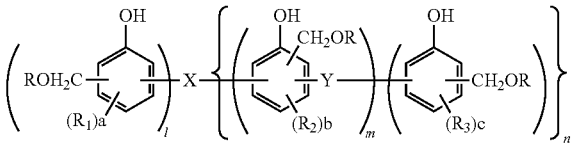

(In the formula, all Rs may be the same or different and respectively represent a hydrogen atom or *an aliphatic hydrocarbon group that may have an* aromatic hydrocarbon group, hydroxyl group, or [aliphatic hydrocarbon group that may have an] ether group. $R_1$, $R_2$ and $R_3$ may be the same or different and respectively represent a hydrocarbon group, hydrocarbon group containing oxygen atom, hydroxyl group, halogen group or halogenated hydrocarbon group; a and c respectively indicate an integer of 0 or 1 to 3, while b indicates an integer of 0, 1 or 2; l and n respectively indicate an integer of 1 to 3; m indicates an integer of 0, 1 or 2; X indicates a bond group or a single bond; and Y indicates a bivalent alkylene group. If m is 0, however, X is a trivalent to hexavalent bond group and l+n is 3 to 6.)

Under a production method conforming to the present invention, the target substance, or a polynuclear poly(formylphenol) expressed by General Formula (9), is produced by causing the corresponding material, or a polynuclear polyphenol expressed by General Formula (8), to react with hexamethylene tetramine in the presence of an acid and then hydrolyzing the obtained reaction product. This reaction converts the hydroxy methyl group or alkoxy methyl group in the polynuclear polyphenol compound (the material compound) expressed by the aforementioned General Formula (8) and provides the target substance, or a polynuclear poly(formylphenol) compound expressed by General Formula (9).

Accordingly, with respect to a polynuclear poly (formylphenol) expressed by the aforementioned General Formula (8), l, m, n and Y in the formula may be the same as the corresponding symbols in General Formula (9), while $R_1$, $R_2$, $R_3$, a, b, c and X may be the same as or different from the corresponding symbols in General Formula (9). For example, if X has a monovalent group that undergoes acid decomposition, X may decompose during the reaction as long as the alkoxy methyl group or hydroxy methyl group is formylated and the original polynuclear skeletal is maintained. $R_1$, $R_2$, $R_3$, a, b, c and X may not necessarily be the same as the corresponding symbols in General Formula (9), but it is desirable that they be the same. $R_1$, $R_2$ and $R_3$ may be the same or different, and respectively represent a hydrocarbon group, hydrocarbon group containing oxygen atom, hydroxyl group, halogen group or halogenated hydrocarbon group, while a and c respectively indicate an integer of 0 or 1 to 3; b indicates an integer of 0, 1 or 2; l and n respectively indicate an integer of 1 to 3; m indicates an integer of 0, 1 or 2; X indicates a bond group or a single bond; and Y indicates a bivalent alkylene group. R represents a hydrogen atom or *an aliphatic hydrocarbon group that may have an* aromatic hydrocarbon group, hydroxyl group, or [aliphatic hydrocarbon group that may have an] ether group. If m is 0, however, l+n is 3 to 6.

Specifically, $R_1$, $R_2$, $R_3$, a, b, c, l, m, n, X and Y are the same as what is described above with respect to General Formula (9). Similarly, a desired combination of l, n and m is such that m is 0 and l+n is 3 or 4, or m is 1 and l and n are both 1. Also, substitution groups $R_1$, $R_2$ and $R_3$ should desirably be the same and their substitution positions relative to the OH group should also be the same. If m is 0, the OH group should desirably be in position 4 relative to the bond position of bond group X in the phenyl nucleus. If m is not 0, the OH group should desirably in position 2 relative to the bond positions of bond groups X and Y in the phenyl nucleus. Specifically, R is the same as the corresponding symbol in General Formula (3).

Also, with respect to a polynuclear polyphenol expressed by General Formula (8), the substitution position of the hydroxy methyl group or alkoxy methyl group should desirably be the ortho position or para position relative to the hydroxyl group, and it is more desirable to have a substitution group in other o-position or p-position of the hydroxyl group because it increases the yield of synthesis. However, cases where at least one of $R_1$ $R_2$ and $R_3$ in General Formula (8) is a hydrocarbon having a hydroxyl group, ether group or halogen group (bromine, chlorine, etc.,) in the α-position, or specifically a hydroxy methyl group or alkoxy methyl group having such characteristics, are not desirable. Examples of a polynuclear polyphenol expressed by General Formula (8) include, among others, compounds expressed by General Formulas (20), (21) and (22) specified below.

General Formula (20)

[Chemical 32]

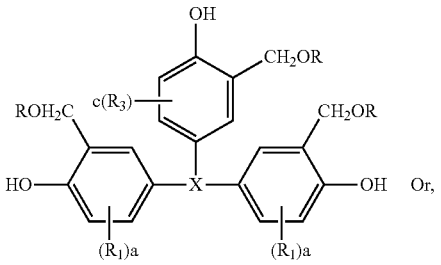

-continued

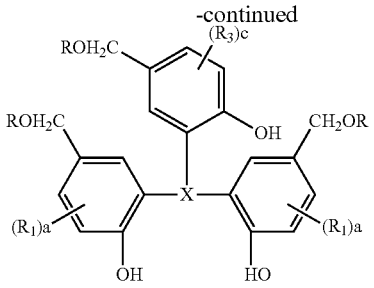

(In the formula, X is a trivalent bond group, m is 0, and l+n is 3, according to General Formula (8).)

General Formula (21)

[Chemical 33]

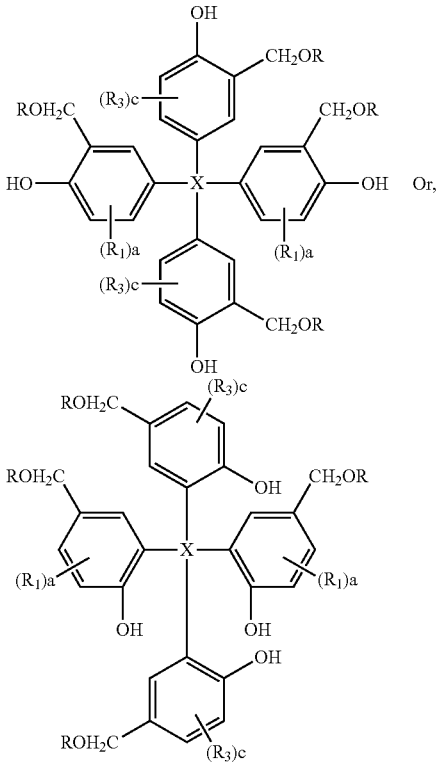

(In the formula, X is a tetravalent bond group, m is 0, and l+n is 4, according to General Formula (8).)

General Formula (22)

[Chemical 34]

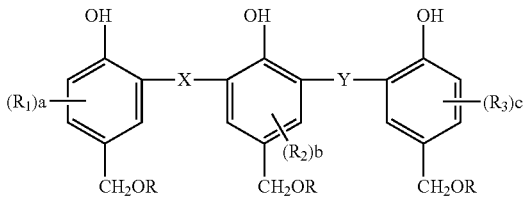

(In the formula, X is a bivalent bond group, m is 1, and l and n are 1, according to General Formula (8).)

On the other hand, R is a hydrogen atom or *an aliphatic hydrocarbon group that may have an* aromatic hydrocarbon group, hydroxyl group, or [aliphatic hydrocarbon group that may have an] ether group, where the *aliphatic hydrocarbon group that may have an* aromatic hydrocarbon group, hydroxyl group, or [aliphatic hydrocarbon group that may have an] ether group, should desirably be a substituted or unsubstituted saturated aliphatic hydrocarbon group such as an alkyl group, alkoxy alkyl group or phenyl alkyl group, etc., where a primary or secondary substituted or unsubstituted alkyl group is desirable. This alkyl group may be an alkyl group with a carbon atom number of 1 to 20, or desirably an alkyl group of straight or branched chain with a carbon atom number of 1 to 10 or cycloalkyl group with a carbon atom number of 5 to 10. Specific examples include methyl, ethyl and cyclohexyl, among others.

Accordingly, specific compounds corresponding to the material compound used in a production method conforming to the present invention, or a polynuclear hydroxy methyl phenol or polynuclear alkoxy methyl phenol expressed by General Formula (8), include the following, for example:

1-[α-methyl-α-(3-hydroxymethyl-5-methyl-4-hydroxyphenyl)ethyl]-4-[α,α-bis(3-hydrox ymethyl-5-methyl-4-hydroxyphenyl)ethyl]benzene, 1-[α-methyl-α-(3-methoxymethyl-5-methyl-4-hydroxyphenyl)ethyl]-4-[α,α-bis(3-methox ymethyl-5-methyl-4-hydroxyphenyl)ethyl]benzene, and 1-[α-methyl-α-(3-butoxymethyl-5-methyl-4-hydroxyphenyl)ethyl]-4-[α,α-bis(3-butoxym ethyl-5-methyl-4-hydroxyphenyl)ethyl]benzene By using a production method conforming to the present invention, a hydroxy methyl group or alkoxy methyl group bonding with an aromatic ring can be formylated without using the Duff reaction, which is a conventional method known to introduce a formyl group to an aromatic ring and where an unsubstituted benzene ring is directly formylated. Although the mechanism of this reaction is not clear, it is estimated that Schiff's base or other base is generated as an intermediate product, which is then formylated through hydrolysis.

A production method conforming to the present invention, pertaining to an example where 4,4'-methylene bis(2-methyl-6-hydroxymethylphenol) is caused to react with hexamethylene tetramine in the presence of an acid and the obtained reaction product is hydrolyzed to produce 4,4'-methylene bis(2-methyl-6-formylphenol), is expressed by Reaction Formula (2) specified below.

[Reaction Formula (2)]

[Chemical 35]

First reaction (reaction with hexamethylene tetramine)

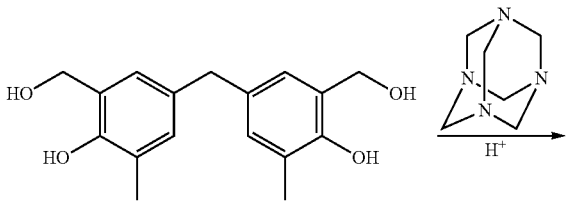

-continued

Reaction product

Second reaction (hydrolysis)

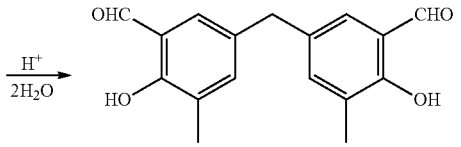

Also, an example where

1-[α-methyl-α-(3-hydroxymethyl-5-methyl-4-hydroxyphenyl)ethyl]-4-[α,α-bis(3-hydrox ymethyl-5-methyl-4-hydroxyphenyl)ethyl]benzene (Chemical Formula 15) is caused to react with hexamethylene tetramine in the presence of an acid and the obtained reaction product is hydrolyzed to produce 1-[α-methyl-α-(3-formyl-5-methyl-4-hydroxyphenyl)ethyl]-4-[α,α-bis(3-formyl-5-methy 1-4-hydroxyphenyl)ethyl]benzene (Chemical Formula 16), is expressed by Reaction Formula (3) specified below.

Reaction Formula (3)

[Chemical 36]

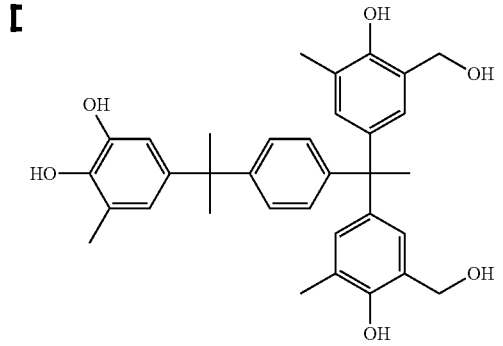

Chemical Formula 15

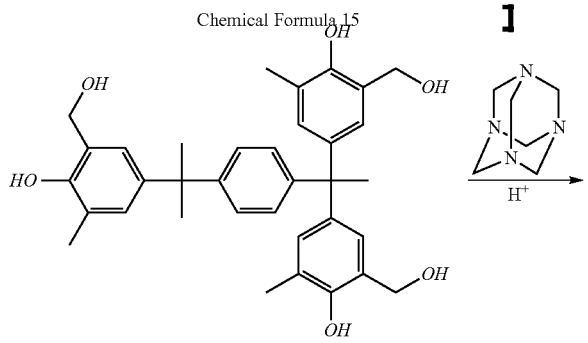

*Chemical Formula 15*

Reaction Products

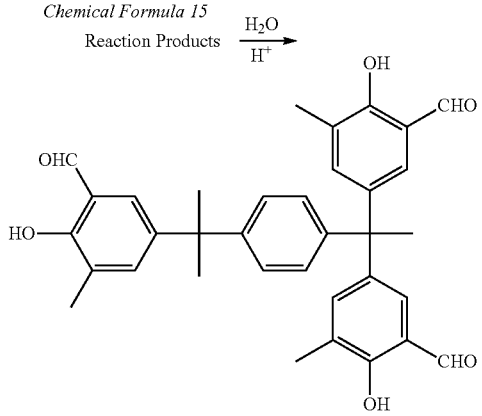

Chemical Formula 16

Under a production method conforming to the present invention, where a polynuclear poly(hydroxymethylphenol) or polynuclear poly(alkoxymethylphenol) expressed by the aforementioned General Formula (1) is caused to react with hexamethylene tetramine in the presence of an acid, acids that can be used include: hydrochloric acid, sulfuric acid, phosphoric acid and other mineral acids; p-toluene sulfonic acid and other organic sulfonic acids; clay, acid clay, zeolite and other silica-alumina solid catalysts; tin chloride, iron chloride, boron fluoride and other Lewis acids; acetic acid, formic acid, oxalic acid, benzoic acid and other aliphatic or aromatic organic carbonic acids as well as trifluoroacetic acids, trichloroacetic acids, tribromoacetic acid, monofluoroacetic acid, monochloro acetic acid, fluorobenzoic acid and other halogenated organic carbonic acids; and boric acid and other inorganic weak acids.

Among the above, organic carbonic acids and boric acids are desirable, of which liquid halogenated organic carbonic acids are particularly desirable.

The amount of acid used in the reaction is affected by the type of acid, and specifically the range of amounts of acid to be added and the optimal amount of acid vary accordingly. Normally, however, around 0.1 to 100 mols, or preferably around 1 to 50 mols, of acid is added relative to 1 mol of polynuclear poly(hydroxymethylphenol) or polynuclear poly (alkoxymethylphenol). For example, if the polynuclear poly (hydroxymethylphenol) or polynuclear poly(alkoxymethylphenol) is a bisphenol expressed by the aforementioned General Formula (3), and trifluoroacetic acid is used, then the amount of trifluoroacetic acid should be in a range of around 1 to 30 mols, or preferably in a range of 5 to 20 mols, relative to 1 mol of bisphenol.

In another example where the polynuclear poly(hydroxymethylphenol) or polynuclear poly(alkoxymethylphenol) expressed by the aforementioned General Formula (1) is a polynuclear poly(hydroxymethylphenol) or polynuclear poly(alkoxymethylphenyl) having three or more hydroxy-substituted phenyl nuclei as expressed by the aforementioned General Formula (8), and trifluoroacetic acid is used, then the amount of trifluoroacetic acid should be in a range of $(l+m+n)\times 0.5$ mols to $(l+m+n)\times 15$ mols, or preferably in a range of around $(l+m+n)\times 2.5$ mols to $(l+m+n)\times 10$ mols, relative to 1 mol of polynuclear poly(hydroxymethylphenol) or polynuclear poly(alkoxymethylphenol). If $(l+m+n)$ is 3, for example, the aforementioned preferable range is from 7.5 mols to 30 mols. If $(l+m+n)$ is 4, the preferable range is from 10 mols to 40 mols.

Also, the form of hexamethylene tetramine is not limited, and it can be a hexamethylene tetramine produced by adding ammonia and formaldehyde, both of which are materials for producing hexamethylene tetramine, in the reaction matrix. The amount of hexamethylene tetramine is not specifically limited as long as it is equivalent to or greater than the total mols of $l+m+n$ in the formula relative to 1 mol of polynuclear poly(hydroxymethylphenol) or polynuclear poly(alkoxymethylphenol). However, adding hexamethylene tetramine excessively reduces the volumetric efficiency, and thus normally, the amount of hexamethylene tetramine should be in a range of 10 mols or less, or preferably in a range of $(l+m+n)\times 1.05$ mols to $(l+m+n)\times 1.5$ mols.

For example, if the polynuclear poly(hydroxymethylphenol) or polynuclear poly(alkoxymethylphenol) is a bisphenol expressed by the aforementioned General Formula (3), then the amount of hexamethylene tetramine is not specifically limited as long as it is 2 mols or more relative to 1 mol of bisphenol. However, adding hexamethylene tetramine excessively reduces the volumetric efficiency, and thus normally its amount should be in a range of 2 to 10 mols, or preferably in a range of 2 to 5 mols, or more preferably in a range of 2.1 to 3 mols.

In another example where the polynuclear poly(hydroxymethylphenol) or polynuclear poly(alkoxymethylphenol) is a polynuclear poly(hydroxymethylphenol) or polynuclear poly(alkoxymethylphenyl) having three or more hydroxy-substituted phenyl nuclei as expressed by the aforementioned General Formula (8), and $(l+m+n)$ is 3, then the amount of hexamethylene tetramine should be in a range of 3.1 to 4.5 mols. If $(l+m+n)$ is 4, it should be in a range of 4.2 to 6 mols.

A solvent may or may not be used in the reaction. A solvent is not particularly necessary as long as the reaction materials are dissolved and the reaction composition can be agitated. If the acid or any material used has a high melting point, or the reaction liquid has high viscosity at the reaction temperature, or otherwise agitation is difficult, it is desirable to use a solvent.

The solvent to be used is not specifically limited as long as it does not inhibit the reaction. Examples include: ether, diethyl ether, tetrahydrofuran and other chain or cyclic aliphatic ethers; ethyl acetate, n-butyl acetate and other desirably primary or secondary aliphatic esters; methanol, ethanol, butanol and other low-grade aliphatic alcohols with a carbon number of 1 to 4; cyclohexanol and other alicyclic alkyl alcohols; toluene, xylene, ethyl benzene and other aromatic hydrocarbons; and mixtures thereof. Among others, aromatic hydrocarbons are desirable.

As for the reaction, the method or order in which to introduce the reaction materials are not limited, and any method or order can be selected as deemed appropriate according to the properties, etc., of the materials used. For example, the material, or a polynuclear poly(hydroxymethylphenol) or polynuclear poly(alkoxymethylphenol) expressed by the aforementioned General Formula (1), can be added to a solution where the acid, hexamethylene tetramine and solvent can coexist; or the acid and hexamethylene tetramine can be added to a solution where the polynuclear poly(hydroxymethylphenol) or polynuclear poly(alkoxymethylphenol) and solvent can coexist; or the acid can be added to a solution where the polynuclear poly(hydroxymethylphenol) or polynuclear poly(alkoxymethylphenol), hexamethylene tetramine and solvent can coexist. If any organic carbonic acid is used as the acid, it is desirable to add the material, or polynuclear poly(hydroxymethylphenol) or polynuclear poly (alkoxymethylphenol), to a solution where the organic carbonic acid and hexamethylene tetramine coexist.

The reaction temperature and pressure are not specifically limited as long as the reaction can progress smoothly, but the reaction temperature is normally in a range of −50 to 150° C., or preferably in a range of 0 to 110° C., or more preferably in a range of 50 to 90° C. The reaction pressure is in a range of slight decompression to slight pressurization, and preferably around a normal pressure.

Under a production method conforming to the present invention, the target substance, or a polynuclear poly (formylphenol) expressed by the aforementioned General Formula (2), is obtained by causing a polynuclear poly(hydroxymethylphenol) or polynuclear poly(alkoxymethylphenol) expressed by the aforementioned General Formula (1) to react with hexamethylene tetramine in the presence of an acid and then hydrolyzing the obtained intermediate reaction product.

In the hydrolysis reaction, the intermediate reaction product obtained from the reaction with hexamethylene tetramine may be separated by means of filtering, etc., or refined further as necessary. From the viewpoint of improved efficiency and yield of reaction, however, it is desirable to directly use the aforementioned mixture obtained by the reaction with hexamethylene tetramine. Also, a catalyst may or may not be used in the reaction, but desirably a catalyst should be used. The catalyst to be used may be an acid catalyst or alkali catalyst. If the material, or a polynuclear poly(hydroxymethylphenol) or polynuclear poly(alkoxymethylphenol) expressed by the aforementioned General Formula (1), contains primary ester in its phenyl nucleus or bond group X, then use of an acid catalyst is desirable because the material is easy to hydrolyze in the presence of an alkali. It is also possible, for example, to use the same acid employed in the reaction with hexamethylene tetramine directly as the catalyst for hydrolysis. In this case, more acid may be added if the reaction is slow.

Or, any known acid catalyst may be added on top of the aforementioned acid. However, exercise caution because in the case of a strong acid, adding it excessively will cause the formyl group or ester group to break down and the yield will drop.

The amount of acid to be used should normally be in a range of 0.1 to 100 mols, or preferably in a range of around 1 to 20 mols, relative to 1 mol of polynuclear poly(hydroxymethylphenol) or polynuclear poly(alkoxymethylphenol) expressed by the aforementioned General Formula (1).

Accordingly, examples of the acid catalyst that can be used in hydrolysis include: hydrochloric acid, sulfuric acid and other mineral acids; p-toluene sulfonic acid and other organic sulfonic acids; and phosphoric acid, acetic acid, formic acid, trifluoroacetic acid and other organic carbonic acids. Examples of the alkali catalyst that can be used in hydrolysis include: sodium hydroxide, potassium hydroxide and other inorganic bases; and tetramethyl ammonium hydroxide and other organic bases.

At the time of hydrolysis reaction, the amount of water in the reaction composition is not specifically limited as long as the reaction can progress smoothly. From the viewpoint of volumetric efficiency, etc., however, the amount of water should normally be in a range of $(l+m+n)\times 1$ mols to $(l+m+n)\times 40$ mols, or preferably in a range of $(l+m+n)\times 10$ mols to $(l+m+n)\times 25$ mols, relative to 1 mol of the material polynuclear poly(hydroxymethylphenol) or polynuclear poly(alkoxymethylphenol) expressed by the aforementioned General Formula (1). If the polynuclear poly(hydroxymethylphenol) or polynuclear poly(alkoxymethylphenol) is a bisphenol expressed by the aforementioned General Formula (3), for example, the amount of water is normally in a range of 2 to 80 mols, or preferably in a range of 20 to 50 mols, relative to 1 mol of the material bisphenol.

The reaction temperature and pressure are not specifically limited as long as the reaction can progress smoothly, but the reaction temperature is normally in a range of −50 to 150° C., or preferably in a range of 0 to 100° C., or more preferably in a range of 50 to 80° C. The reaction pressure is in a range of slight decompression to slight pressurization, and preferably around a normal pressure.

After the reaction, according to known methods, the target composition or refined product may be collected at high yield from the mixture obtained from the reaction. If the target substance in the mixture obtained from the reaction has precipitated as crystal, for example, then the target substance may be filtered out directly. If the target substance has not precipitated as crystal, then a poor solvent may be added to the mixture obtained from the reaction to precipitate and separate the target substance.

At this time, neutralization using alkali water of the acid catalyst in the mixture obtained from the reaction, or neutralization of the acid using an alkali catalyst, is not always required. If an acid catalyst is used, for example, it is possible to add to the mixture obtained from the reaction an appropriate amount of sodium hydroxide or other alkali water needed to neutralize the acid catalyst until the pH becomes approx. 4 to 7, and then perform the aforementioned separation/precipitation operation of the target substance, such as adding a solvent that can be separated from water, such as toluene, xylene, methyl isobutyl ketone or ether, to cause the water layer to separate from the oil layer containing the target substance. Or, the target substance may be precipitated and separated without neutralizing the acid catalyst in the mixture obtained from the reaction, followed by washing of the obtained target composition to remove the acid.

Particularly when the acid used in the reaction is trifluoroacetic acid or other acid of low boiling point, the latter method lets you distill and collect the acid catalyst in the mixture obtained from the reaction because the acid catalyst has not been neutralized, and utilize the collected acid catalyst directly.

If necessary in refining the target substance, after the aforementioned operation the obtained target composition may be further mixed with water or toluene, xylene, methyl isobutyl ketone, ether or other solvent that can be separated from water to dissolve the target composition, after which the water layer can be separated and oil layer washed in order to obtain the oil layer containing the target substance.

Next, the solvent is distilled away from the obtained oil layer, and then a crystallization solvent is added to crystallize the target substance and filter out the crystal. If the purity of the crystal is low, the aforementioned recrystallization operation may be repeated once or multiple times as necessary.

The polynuclear polyphenol expressed by General Formula (1), used as the direct material in a production method conforming to the present invention, is not specifically limited in terms of how it is produced. However, if, for example, the polynuclear poly(hydroxymethylphenol) or polynuclear poly(alkoxymethylphenol) expressed by the aforementioned General Formula (1) is a bisphenol expressed by the aforementioned General Formula (3), then the material can be easily obtained from a bisphenol expressed by General Formula (5) specified below by means of any known hydroxy methylation reaction or alkoxy methylation reaction, among others.

General Formula (5)

[Chemical 37]

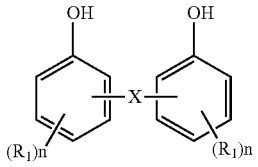

(In the formula, $R_1$, n and X indicate the same things represented by the corresponding symbols in General Formula (3).)

Examples of the reaction product include a bis(hydroxymethylphenol) expressed by General Formula (6) specified below, being a bisphenol expressed by General Formula (3) where R is a hydrogen atom.

General Formula (6)

[Chemical 38]

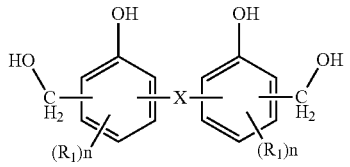

(In the formula, $R_1$, n and X indicate the same things represented by the corresponding symbols in General Formula (3).)

If the bisphenol is 4,4'-methylene bis(2-methylphenol), the bisphenol can be caused to react with formaldehyde in the presence of an alkali catalyst, as illustrated by Reaction Formula (4) specified below. It is economically desirable to use as the materials those compounds that can be produced easily from inexpensive materials such as formaldehyde and alkali. It is more desirable to use a material bisphenol whose hydroxyl group has no substitution group in only one of the o-position and p-position, and has a substitution group in all other positions, because it will increase the yield and facilitate production of the target substance at high purity.

Also, the bis(alkoxymethylphenol) can be produced easily by causing the obtained bis(hydroxymethylphenol) to further react with an alcohol expressed by General Formula (7) specified below in the presence of an acid catalyst, as illustrated by Reaction Formula (5) specified below. As for the alcohol expressed by General Formula (7), primary or secondary alcohol is desirable, such as methanol, n-butanol, methoxy ethanol, ethylene glycol, etc.

Reaction Formula (4)

[Chemical 39]

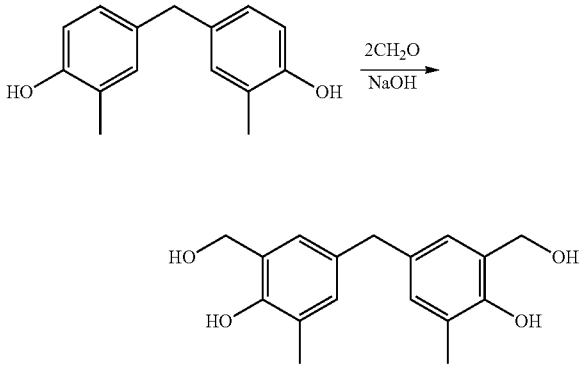

[Chemical 40]

R—OH General Formula (7)

(In the formula, R represents an *aliphatic hydrocarbon group that may have an* aromatic hydrocarbon group, hydroxyl group, or [aliphatic hydrocarbon group that may have an] ether group.)

Reaction Formula (5)

[Chemical 41]

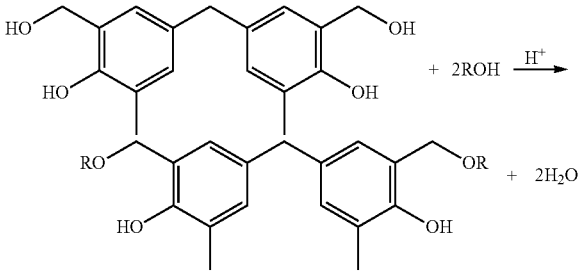

(In the formula, R represents an *aliphatic hydrocarbon group that may have an* aromatic hydrocarbon group, hydroxyl group, or [aliphatic hydrocarbon group that may have an] ether group.)

Also, if the polynuclear poly(hydroxymethylphenol) or polynuclear poly(alkoxymethylphenol) expressed by the aforementioned General Formula (1) is a polynuclear poly (hydroxymethylphenol) or polynuclear poly(alkoxymethylphenyl) having three or more hydroxy-substituted phenyl nuclei as expressed by the aforementioned General Formula (8), the material can be easily obtained from a polynuclear polyphenol expressed by General Formula (10) specified below by means of any known hydroxy methylation reaction or alkoxy methylation reaction, among others.

General Formula (10)

[Chemical 42]

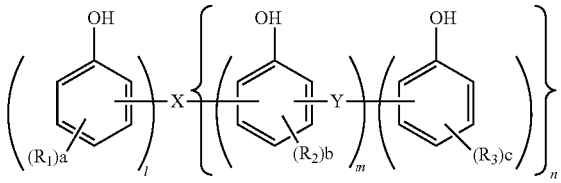

(In the formula, $R_1$, $R_2$, $R_3$, a, b, c, l, m, n, X and Y indicate the same things represented by the corresponding symbols in General Formula (8), and at least one of the o-position and p-position of the hydroxyl group is not substituted.)

As for the reaction product, if R is a hydrogen atom in the polynuclear polyphenol expressed by the aforementioned General Formula (8), for example, then the polynuclear poly (hydroxymethylphenol) is expressed by General Formula (11) specified below.

General Formula (11)

[Chemical 43]

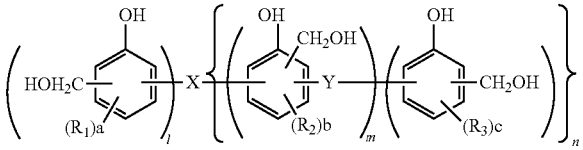

(In the formula, $R_1$, $R_2$, $R_3$, a, b, c, l, m, n, X and Y indicate the same things represented by the corresponding symbols in General Formula (8), and the substitution position of the hydroxy methyl group is the opposition or p-position relative to the hydroxyl group.)

Such polynuclear poly(hydroxymethylphenol) can be produced easily by any known method, such as the method described in Japanese Patent Laid-open No. 2003-300922 whereby a polynuclear polyphenol is caused to react with formaldehyde in the presence of an alkali catalyst. For example, Reaction Formula (6) specified below illustrates an example where the polynuclear polyphenol is 1-[α-methyl-α-(5-methyl-4-hydroxyphenyl)ethyl]-4-[α,α-bis(5-methyl-4-hydroxyphenyl)ethyl]benzene. It is economically desirable to use as the materials those compounds that can be produced easily from inexpensive materials such as formaldehyde and alkali. It is more desirable to use a material polynuclear polyphenol, expressed by General Formula (10), whose hydroxyl group has a hydrogen atom in only one of the substitution groups corresponding to the opposition and p-position, because it will increase the yield and facilitate production of the target substance at high purity.

On the other hand, the polynuclear poly(alkoxymethylphenol) can be produced easily by, for example, causing the polynuclear poly(hydroxymethylphenol) obtained above to further react with an alcohol expressed by General Formula (12) specified below in the presence of an acid catalyst. The desirable alcohols expressed by General Formula (12), and specific examples, are the same as those discussed in relation to General Formula (7). Reaction Formula (7) specified below illustrates an example of such production method, where the polynuclear poly(hydroxymethylphenol) obtained from Reaction Formula (6) specified below is a tri(hydroxymethyl) compound or specifically 1-[α-methyl-α-(3-hydroxymethyl-5-methyl-4-hydroxyphenyl)ethyl]-4-[α,α-bis(3-hydrox y methyl-5-methyl-4-hydroxy phenyl)ethyl]benzene.

Reaction Formula (6)

[Chemical 44]

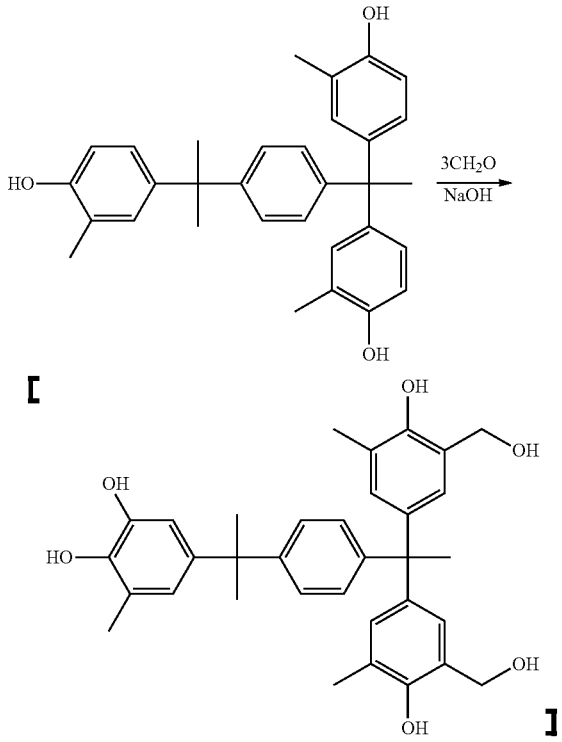

-continued

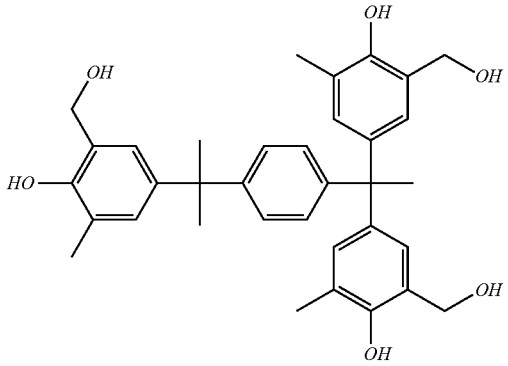

Reaction Formula (7)

[Chemical 45]

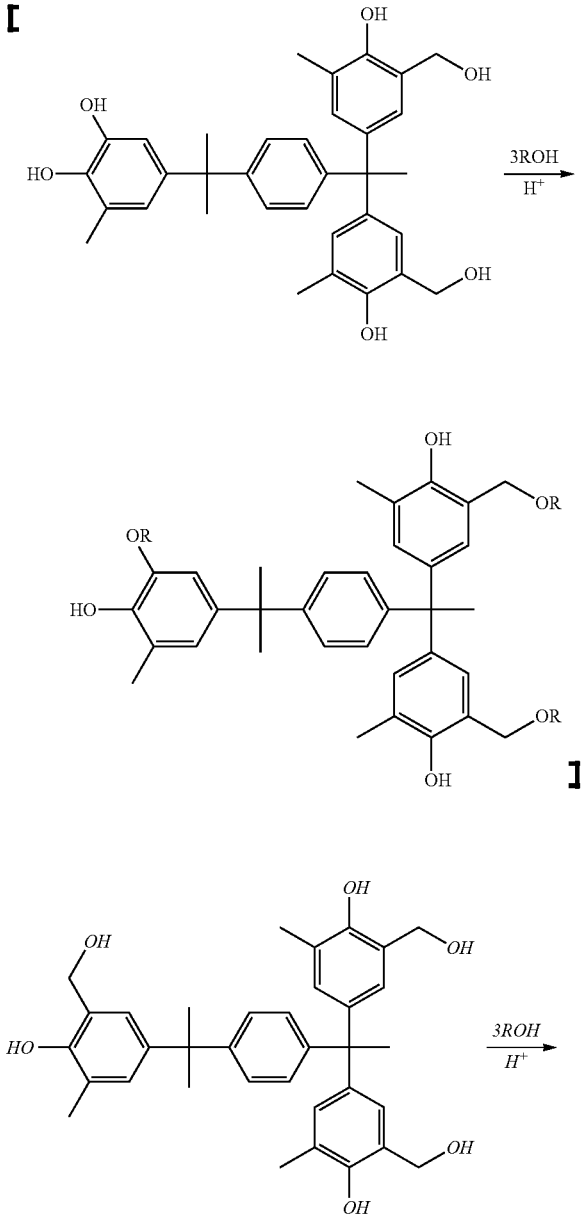

-continued

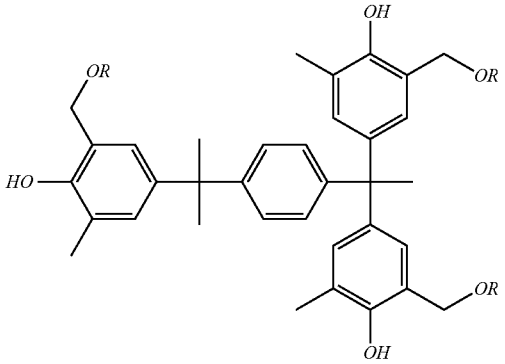

(In the formula, R represents an *aliphatic hydrocarbon group that may have an* aromatic hydrocarbon group, hydroxyl group, or [aliphatic hydrocarbon group that may have an] ether group.)

[Chemical 46]

R—OH General Formula (12)

(In the formula, R represents an *aliphatic hydrocarbon group that may have an* aromatic hydrocarbon group, hydroxyl group, or [aliphatic hydrocarbon group that may have an] ether group.)

Also, under a production method conforming to the present invention, the selection of whether to use a polynuclear poly (hydroxymethylphenol) or polynuclear poly(alkoxymethylphenol) corresponding to the target compound is not specifically limited when a polynuclear polyphenol expressed by General Formula (1) is used as the starting material. A desired material can be determined as deemed appropriate by considering the production method, ease of achieving high purity, stability and toxicity of the compound, reaction selectivity, and the like.

EFFECTS OF THE INVENTION

According to a production method conforming to the present invention, a polynuclear formyl phenol which is useful as a resist material, polymerization catalyst or resin or other material can be produced with ease and at high yield and high volumetric efficiency by causing a polynuclear polyphenol expressed by General Formula (1) to react with hexamethylene tetramine in the presence of an acid and then hydrolyze the reaction product.

Furthermore, the material polynuclear poly(hydroxymethylphenol) or polynuclear poly(alkoxymethylphenol) can be produced easily from the corresponding polynuclear polyphenol depending on the substitution position of the hydroxy methyl group or alkoxy methyl group as well as the details of substitution numbers a, b, c and substitution groups $R_1$, $R_2$, $R_3$, X and Y, which allows for production of a polynuclear poly(formylphenol) consistently from a polynuclear polyphenol in an industrial setting with ease and at high yield and high efficiency.

BEST MODE FOR CARRYING OUT THE INVENTION

EXAMPLES

Example 1

Synthesis of 4,4'-methylene bis(2-methyl-6-formylphenol) (Chemical Formula 17)

1140.0 g (10.0 mols) of trifluoroacetic acid was put in a four-way flask with a capacity of 5 liters and the reaction container was substituted by nitrogen, after which 315.0 g (2.25 mols) of hexamethylene tetramine was added at a temperature of approx. 30° C., and then 288.0 g of 4,4'-methylene bis(2-methyl-6-hydroxymethylphenol) (1.0 mol; purity 93% based on high-speed liquid chromatograph (HPLC)) was added under agitation over 3 hours at a temperature of 40° C. to cause reaction. After the entire amount of the material had been added, the temperature was raised to 85° C., and then the mixture was further agitated for 3 hours as a post-reaction. After the reaction, the obtained liquid was partially collected and hydrolyzed, and then analyzed based on HPLC. As a result, the main component that appeared to be the target substance had a composition ratio of 70%. Next, 800.0 g of water was added to the liquid obtained from the reaction to implement hydrolysis reaction for 1 hour at a temperature of 60° C. Crystal precipitated during this reaction. After the reaction, 1471.0 g of 16% aqueous sodium hydroxide solution was added to neutralize the obtained mixture liquid, and then 50 g of methyl isobutyl ketone and 50 g of methanol were added further, after which the mixture was cooled and precipitated crystal was filtered out to obtain 302.3 g of a composition. The obtained composition was put in a four-way flask with a capacity of 2 liters, and 369.2 g of methyl isobutyl ketone and 255.6 g of toluene were added, and then the mixture was maintained at a temperature of 70° C. and agitated for 30 minutes in a slurry state. The mixture was cooled and precipitated crystal was filtered out and dried to obtain 196.8 g of yellow powder crystal having a purity of 95.8% based on HPLC. The yield with respect to 4,4'-methylene bis(2-methyl-6-hydroxymethylphenol) was 69.3%. Based on the results of NMR and mass spectrometry, the obtained crystal was confirmed to be the target substance.

Chemical Formula 17

[Chemical 47]

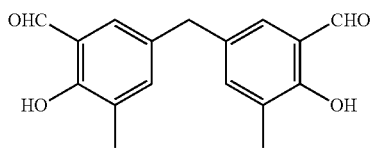

Melting point: 155.4° C. (based on peak top by differential scanning calorimetry)

Molecular weight: 283 $(M—H)^-$ (by mass spectrometry LC-MS $(APCI^-)$)

Proton NMR identification result (400 MHz, solvent: DMSO-d6, internal standard: tetramethyl silane)

TABLE 1

| Shift value (ppm) | Proton number | Signal | Attribution |
|---|---|---|---|
| 2.17 | 6 | s | —$CH_3$ |
| 3.86 | 2 | s | —$CH_2$— |
| 7.37 to 7.44 | 4 | m | Ph—H |
| 10.00 | 2 | s | Ph—OH |
| 10.88 | 2 | s | —CHO |

TABLE 2

| Shift value (ppm) | Proton number | Signal | Attribution |
|---|---|---|---|
| 2.23 | 6 | s | —$CH_3$ |
| 3.90 | 2 | s | —$CH_2$— |
| 7.20 to 7.44 | 4 | m | Ph—H |
| 9.98 | 2 | s | Ph—OH |
| 10.96 | 2 | s | —CHO |

Example 2

Synthesis of 2,2'-methylene bis(4-methyl-6-formylphenol) from bis(hydroxymethylphenol) Compound (Chemical Formula 18)

546.4 g (4.8 mols) of trifluoroacetic acid was put in a four-way flask with a capacity of 2 liters and the reaction container was substituted by nitrogen, after which 123.2 g (0.88 mol) of hexamethylene tetramine was added at a temperature of approx. 30° C., and then 115.3 g of 2,2'-methylene bis(4-methyl-6-hydroxymethylphenol) (0.4 mol; purity 89% based on HPLC) was added under agitation over 2 hours at a temperature of 60° C. to cause reaction. After the entire amount of the material had been added, the temperature was raised to 85° C., and then the mixture was further agitated for 4 hours as a post-reaction. After the reaction, the obtained mixture liquid was partially collected and then analyzed based on HPLC in the same manner as in Example 1. As a result, the main component that appeared to be the target substance had a composition ratio of 76%.

Next, 320.0 g of water was added to the liquid obtained from the reaction to implement hydrolysis reaction for 1 hour at a temperature of 60° C. Crystal precipitated during this reaction. After the reaction, 830.0 g of 16% aqueous sodium hydroxide solution was added to neutralize the obtained mixture liquid, and then 220.0 g of toluene and 280.0 g of cyclohexane were added further, after which the mixture was cooled and precipitated crystal was filtered out and dried to obtain 81.5 g of yellow powder having a purity of 95.6% based on HPLC. The yield with respect to 2,2'-methylene bis(4-methyl-6-hydroxymethylphenol) was 71.7%.

Based on the results of NMR and mass spectrometry, the obtained crystal was confirmed to be the target substance.

Chemical Formula 18

[Chemical 48]

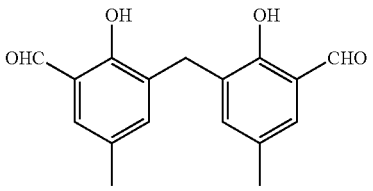

Melting point: 160.3° C., 168.5° C. (based on peak top by differential scanning calorimetry)

Molecular weight: 283 $(M—H)^-$ (by mass spectrometry LC-MS $(APCI^-)$)

Proton NMR identification result (400 MHz, solvent: DMSO-d6, internal standard: tetramethyl silane)

Example 3

Synthesis of 2,2'-methylene bis(4-methyl-6-formylphenol) from bis(alkoxymethylphenol) Compound 13.7 g (0.12 mol) of trifluoroacetic acid was put in a four-way flask with a capacity of 200 ml and the reaction container was substituted by nitrogen, after which 2.8 g (0.02 mol) of hexamethylene tetramine was added at a temperature of 30° C., and then 6.3 g of 2,2'-methylene bis(4-methyl-6-methoxymethylphenol) (0.01 mol; purity 90% based on HPLC) was added under agitation over 2 hours at a temperature of 60° C. to cause reaction. After the entire amount of the material had been added, the temperature was raised to 85° C., and then the mixture was further agitated for 4 hours as a post-reaction. After the reaction, the obtained liquid was partially collected and analyzed based on HPLC in the same manner as in Example 2. As a result, the main component corresponding to the target substance had a composition ratio (area %) of 73%.

Example 4

Synthesis of 4,4'-methylene bis(2,5-dimethyl-6-formylphenol) (Chemical Formula 17)

171.0 g (1.5 mol) of trifluoroacetic acid was put in a four-way flask with a capacity of 1 liter and the reaction container was substituted by nitrogen, after which 47.3 g (0.34 mol) of hexamethylene tetramine was added at a temperature of approx. 25° C., and then 47.4 g (0.15 mol) of 4,4'-methylene bis(2,5-dimethyl-6-hydroxymethylphenol) was added under agitation over 2.5 hours at a temperature of 50° C. to cause reaction. After the entire amount of the material had been added, the temperature was raised to 80° C., and then the mixture was further agitated for 20 hours as a post-reaction. Next, 150.0 g of water was added to the mixture liquid obtained from the reaction to implement hydrolysis reaction for 1 hour at a temperature of 70° C. (crystal precipitated during this reaction). 245.7 g of 16% aqueous sodium hydroxide solution was added to neutralize the obtained mixture liquid, which was then kept at a temperature of 80° C. for 1 hour. Thereafter, the mixture was cooled and precipitated crystal was filtered out to obtain 72.3 g of coarse crystal. Next, the obtained coarse crystal was put in a four-way flask with a capacity of 1 liter, and then 70.0 g of methyl isobutyl ketone and 50.0 g of toluene were added and the mixture was kept at a temperature of 80° C. for 1 hour (the solution was in a slurry state), after which the mixture was cooled and precipitated crystal was filtered out and dried to obtain 45.3 g of yellow powder having a purity of 94.6% based on HPLC.

The yield with respect to 4,4'-methylene bis(2,5-dimethyl-6-hydroxymethylphenol) was 82.1%.

Based on the results of NMR and mass spectrometry, the obtained crystal was confirmed to be the target substance.

Chemical Formula 19

[Chemical 49]

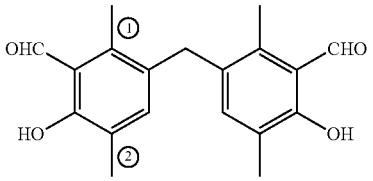

Melting point: 200.7° C. (based on peak top by differential scanning calorimetry)

Molecular weight: 311 $(M—H)^-$ (by mass spectrometry LC-MS $(APCI^-)$)

Proton NMR identification result (400 MHz, solvent: DMSO-d6, internal standard: tetramethyl silane)

TABLE 3

| Shift value (ppm) | Proton number | Signal | Attribution |
|---|---|---|---|
| 2.07 | 6 | s | $—CH_3$ ([2]) |
| 2.46 | 6 | s | $—CH_3$ ([1]) |
| 3.84 | 2 | s | $—CH_2$ |
| 7.00 | 2 | s | Ph—H |
| 10.41 | 2 | s | Ph—OH |
| 12.25 | 2 | s | —CHO |

Comparative Example 1

Synthesis of 4,4'-methylene bis(2-methyl-6-formylphenol) from 4,4'-methylene bis(2-methylphenol) via Duff Reaction (Reaction Formula 8)

13.7 g (0.12 mol) of trifluoroacetic acid was put in a four-way flask with a capacity of 200 ml and the reaction container was substituted by nitrogen, after which 2.8 g (0.02 mol) of hexamethylene tetramine was added at a temperature of approx. 30° C., and then 2.3 g (0.01 mol) of 4,4'-methylene bis(2-methylphenol) was added under agitation over 2 hours at a temperature of 40° C. to cause reaction. After the entire amount of the material had been added, the temperature was raised to 85° C., and then the mixture was further agitated for 3 hours as a post-reaction. After the post-reaction, the obtained liquid was partially collected and analyzed based on HPLC in the same manner as in Example 1. As a result, the main component that appeared to be the target substance had a low selectivity. When the post-reaction was continued for 12 hours and the obtained liquid was analyzed based on HPLC in the same manner, the main component that appeared to be the target substance had a composition ratio (area %) of only 7%.

Reaction Formula (8)

[Chemical 50]

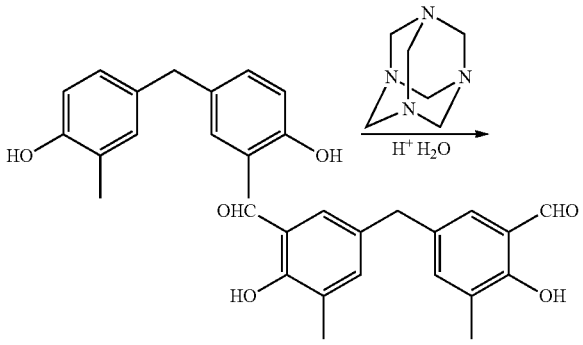

Example 5

Synthesis of 1-[α-methyl-α-(3-formyl-5-methyl-4-hydroxyphenyl)ethyl]-4-[α,α-bis(3-formyl-5-methy 1-4-hydroxyphenyl)ethyl]benzene 410.4 g (3.6 mol) of trifluoroacetic acid was put in a four-way flask with a capacity of 1 liter and the reaction container was substituted by nitrogen, after which 92.4 g (0.66 mol) of hexamethylene tetramine was added at a temperature of approx. 30° C., and then 111.4 g of 1-[α-methyl-α-(3-hydroxymethyl-5-methyl-4-hydroxyphenyl)ethyl]-4-[α,α-bis (3-hydrox ymethyl-5-methyl-4-hydroxyphenyl)ethyl]benzene (0.2 mol; purity 92.4% based on high-speed liquid chromatography (HPLC)) was added under agitation over 2 hours at a temperature of 60° C. to cause reaction. After the entire amount of the material had been added, the temperature was raised to 85° C., and then the mixture was further agitated for 5 hours as a post-reaction.

Next, 240 g of water was added to the mixture liquid obtained from the reaction to implement hydrolysis reaction for 1 hour at a temperature of 60° C. Viscous solids precipitated during this reaction. After the reaction, 220 g of toluene was added to the obtained mixture liquid, which was then heated to a temperature of 70° C. to dissolve the solids and then kept stationary for 10 minutes to separate the water layer. 32.8 g of 16% aqueous sodium hydrochloride solution was added to neutralize the obtained oil layer, and water was added further to agitate the mixture, which was then kept stationary to separate the water layer and the obtained oil layer was decompressed and condensed up to 10 kPa at 70° C. Thereafter, 30 g of ethyl acetate was added and the mixture was cooled to 50° C., and then 200 g of cyclohexane was added further, with the mixture cooled and precipitated crystal filtered out and dried to obtain 52.7 g of light yellow powder (purity 93.2% based on high-speed liquid chromatography). Based on the results of NMR and mass spectrometry, the obtained crystal was confirmed to be the target substance.

Melting point (peak top by differential scanning calorimetry): 143.0° C.

Molecular weight: 549 $(M—H)^-$ (by mass spectrometry LC-MS $(APCI^-)$)

Proton nuclear magnetic resonance analysis method (400 MHz, solvent: DMSO-d6)

[Chemical 51]

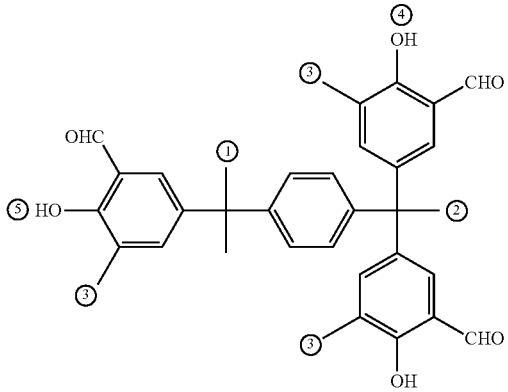

TABLE 4

| 1H-NMR (400 MHz) measurement results (Internal standard: Tetramethyl silane) | | | |
|---|---|---|---|
| Shift value (ppm) | Proton number | Signal | Attribution |
| 1.64 | 6 | s | —$CH_3$ ([1]) |
| 2.11 | 3 | s | —$CH_3$ ([2]) |
| 2.14 | 9 | s | —$CH_3$ ([3]) |
| 6.98 to 7.53 | 10 | m | Ph—H |
| 9.94 | 2 | s | Ph—OH ([4]) |
| 10.02 | 1 | s | Ph—OH ([5]) |
| 10.92 | 3 | s | —CHO |

Example 6

2.85 g (0.025 mol) of trifluoroacetic acid was put in a four-way flask with a capacity of 100 ml and the reaction container was substituted by nitrogen, after which 0.64 g (0.0046 mol) of hexamethylene tetramine was added at a temperature of 30° C., and then 0.77 g of 1-[α-methyl-α-(3-hydroxymethyl-5-methyl-4-hydroxyphenyl)ethyl]4-[α,α-bis(3-hydrox ymethyl-5-methyl-4-hydroxyphenyl)ethyl] benzene (0.00139 mol; purity 92.4% based on high-speed liquid chromatography) was added under agitation over 5 minutes at a temperature of 50° C. to cause reaction. After the entire amount of the material had been added, 2.85 g of toluene was added and the temperature was raised to 85° C., and then the mixture was further agitated for 4 hours as a post-reaction. After the reaction, the obtained liquid was partially collected and hydrolyzed, and then analyzed by high-speed liquid chromatography. As a result, the main component that appeared to be the target substance had a composition ratio (area ratio) of 60.9%.

Comparative Example 2

2.85 g (0.025 mol) of trifluoroacetic acid was put in a four-way flask with a capacity of 100 ml and the reaction container was substituted by nitrogen, after which 0.64 g (0.0046 mol) of hexamethylene tetramine was added at a temperature of 30° C., and then 0.65 g of 1-[α-methyl-α-(3-methyl-4-hydroxyphenyl)ethyl]-4-[α,α-bis(3-methyl-4-hydroxyphenyl)ethyl]benzene (0.00139 mol; purity 97.6% based on HPLC) was added under agitation over 5 minutes at a temperature of 50° C. to cause reaction. After the entire amount of the material had been added, 2.85 g of toluene was added and the temperature was raised to 85° C., and then the mixture was further agitated for 4 hours. However, a lot of material crystal remained undissolved, and therefore the mixture was agitated further for 4 hours as a post-reaction. After the reaction, the obtained liquid was partially collected and hydrolyzed, and then analyzed by high-speed liquid chromatography. As a result, although the material had almost entirely reacted, the main component that appeared to be the target substance had a composition ratio (area ratio) of 18.4%.

What is claimed is:

1. A method for producing a polynuclear poly(formylphenol) expressed by General Formula (2), characterized in that a polynuclear polyphenol expressed by General Formula (1) is caused to react with hexamethylene tetramine in the presence of an acid, and then the obtained reaction product is hydrolyzed:

General Formula (1)

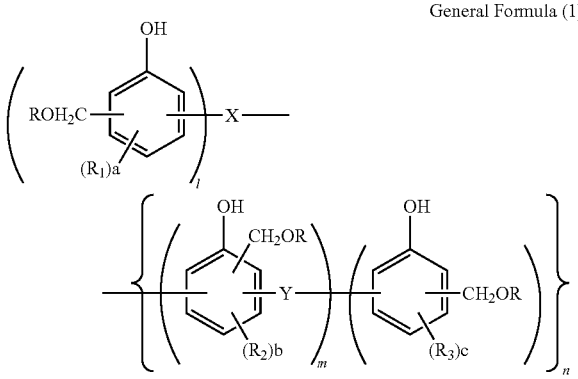

wherein all Rs may be the same or different and respectively represent a hydrogen atom or *an aliphatic hydrocarbon group that may have an* aromatic hydrocarbon group, hydroxyl group, or [aliphatic hydrocarbon group that may have an] ether group; $R_1$, $R_2$ and $R_3$ may be the same or different and respectively represent a hydrocarbon group, hydrocarbon group containing oxygen atom, hydroxyl group, halogen group or halogenated hydrocarbon group; a and c respectively indicate an integer of 0 or 1 to 3, while b indicates an integer of 0, 1 or 2; l and n respectively indicate an integer of 1 to 3; m indicates an integer of 0, 1 or 2; X indicates a bond group or single bond; and Y indicates a bivalent alkylene group;

General Formula (2)

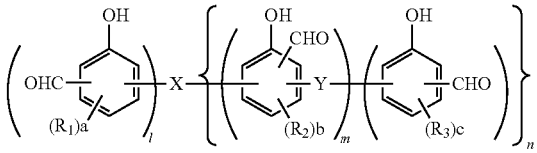

wherein $R_1$, $R_2$, $R_3$, a, b, c, l, m, n, X and Y indicate the same things represented by the corresponding symbols in General Formula (1), wherein the $CH_2OR$'s in General Formula (1) are converted into the CHO's in General Formula (2).

2. The method for producing a polynuclear poly (formylphenol) according to claim 1, wherein, with respect to a polynuclear polyphenol expressed by the aforementioned General Formula (1), if m is 0, X is a bivalent bond group or single bond and l+n is 2 in the formula, then the polynuclear polyphenol is a bisphenol expressed by General Formula (3) specified below, and wherein similarly the polynuclear poly (formylphenol) expressed by the aforementioned General Formula (2) is a bis(formylphenol) expressed by General Formula (4) specified below:

General Formula (3)

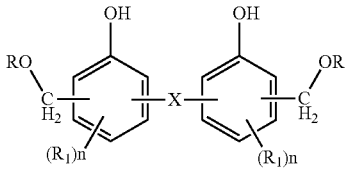

wherein all Rs may be the same or different and respectively represent a hydrogen atom or *an aliphatic hydrocarbon group*

*that may have an* aromatic hydrocarbon group, hydroxyl group, or [aliphatic hydrocarbon group that may have an] ether group, where n indicates an integer of 0 or 1 to 3; both $R_1$s may be the same or different and respectively represent a hydrocarbon group, hydrocarbon group containing oxygen atom, halogenated hydrocarbon group, hydroxyl group or halogen group[.]; X indicates a bivalent bond group or single bond;

General Formula (4)

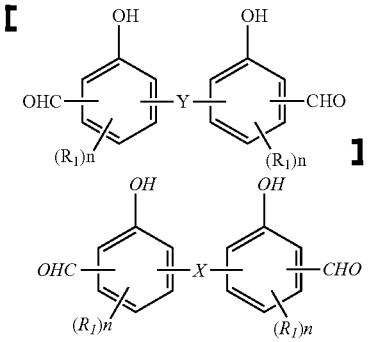

wherein $R_1$, n and X indicate the same things represented by the corresponding symbols in General Formula (3).

3. The method for producing a polynuclear poly (formylphenol) according to claim 2, characterized in that a bis(hydroxymethylphenol) expressed by General Formula (6), being a bisphenol expressed by the aforementioned General Formula (3) where R is a hydrogen atom, is obtained by causing a bisphenol expressed by General Formula (5) to react with formaldehyde in the presence of an alkali catalyst:

General Formula (5)

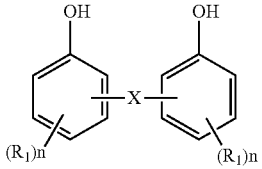

wherein $R_1$, n and X indicate the same things represented by the corresponding symbols in General Formula (3), and at least one of the o-position and p-position of the hydroxyl group is not substituted;

General Formula (6)

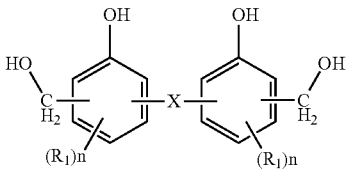

wherein $R_1$, n and X indicate the same things represented by the corresponding symbols in General Formula (3), and the substitution position of the hydroxy methyl group corresponds to the o-position or p-position relative to the hydroxyl group.

4. The method for producing a polynuclear poly (formylphenol) according to claim 2, characterized in that a bis(alkoxymethylphenol), being a bisphenol expressed by the aforementioned General Formula (3) where R is an *aliphatic hydrocarbon group that may have an* aromatic hydrocarbon group, hydroxyl group or [aliphatic hydrocarbon group that may have an] ether group, is obtained by causing a bisphenol expressed by General Formula (5) to react with formaldehyde in the presence of an alkali catalyst and then causing the obtained bis(hydroxymethylphenol) expressed by General Formula (6) to further react with an alcohol expressed by the General Formula (7) specified below in the presence of an acid catalyst:

General Formula (5)

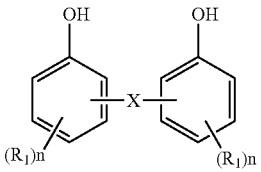

wherein $R_1$, n and X indicate the same things represented by the corresponding symbols in General Formula (3), and at least one of the o-position and p-position of the hydroxyl group is not substituted;

General Formula (6)

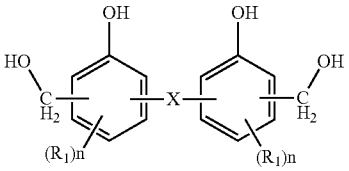

wherein $R_1$, n and X indicate the same things represented by the corresponding symbols in General Formula (3), and the substitution position of the hydroxy methyl group corresponds to the o-position or p-position relative to the hydroxyl group;

R—OH General Formula (7)

wherein R represents an *aliphatic hydrocarbon group that may have an* aromatic hydrocarbon group, hydroxyl group or [aliphatic hydrocarbon group that may have an] ether group.

5. The method for producing a polynuclear poly (formylphenol) according to claim 1, wherein, with respect to a polynuclear polyphenol expressed by the aforementioned General Formula (1), the polynuclear polyphenol where m in the formula indicates an integer of 0, 1 or 2, but where if m is 0, then X is a trivalent to hexavalent bond group and l+n is 3 to 6, is a polynuclear polyphenol expressed by General Formula (8) specified below, and wherein similarly the polynuclear (formylphenol) expressed by the aforementioned General Formula (2) is a polynuclear poly(formylphenol) expressed by General Formula (9) specified below:

General Formula (8)

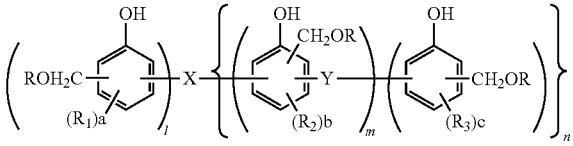

wherein all Rs may be the same or different and respectively represent a hydrogen atom or *an aliphatic hydrocarbon group*

*that may have an* aromatic hydrocarbon group, hydroxyl group, or [aliphatic hydrocarbon group that may have an] ether group, $R_1$, $R_2$ and $R_3$ may be the same or different and respectively represent a hydrocarbon group, hydrocarbon group containing oxygen atom, hydroxyl group, halogen group or halogenated hydrocarbon group; a and c respectively indicate an integer of 0 or 1 to 3, while b indicates an integer of 0, 1 or 2; l and n respectively indicate an integer of 1 to 3; m indicates an integer of 0, 1 or 2; X indicates a bond group or single bond; and Y indicates a bivalent alkylene group[, If] *; if* m is 0, however, X is a trivalent to hexavalent bond group and l+n is 3 to 6;

General Formula (9)

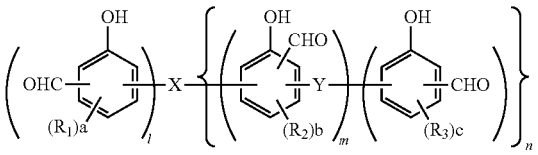

wherein $R_1$, $R_2$, $R_3$, a, b, c, l, m, n, X and Y indicate the same things represented by the corresponding symbols in General Formula (8).

6. The method for producing a polynuclear poly (formylphenol) according to claim 5, characterized in that a polynuclear poly(hydroxymethylphenol) expressed by General Formula (11) specified below, being a polynuclear polyphenol expressed by the aforementioned General Formula (8) where R is a hydrogen atom, is obtained by causing a polynuclear polyphenol expressed by General Formula (10) specified below to react with formaldehyde in the presence of an alkali catalyst:

General Formula (10)

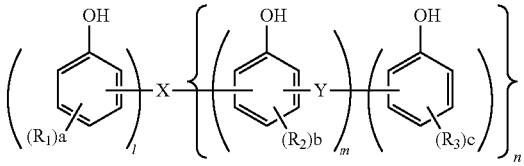

wherein $R_1$, $R_2$, $R_3$, a, b, c, l, m, n, X and Y indicate the same things represented by the corresponding symbols in General Formula (1), and at least one of the o-position and p-position of the hydroxyl group is not substituted; if m is 0, however, X is a trivalent to hexavalent bond group and l+n is 3 to 6;

General Formula (11)

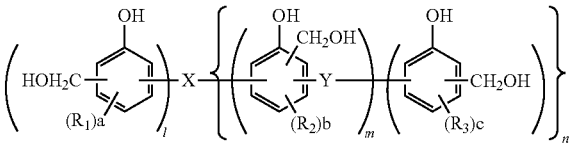

wherein $R_1$, $R_2$, $R_3$, a, b, c, l, m, n, X and Y indicate the same things represented by the corresponding symbols in General Formula (1), and the substituted position of the hydroxy methyl group corresponds to the o-position or p-position relative to the hydroxyl group; if m is 0, however, X is a trivalent to hexavalent bond group and l+n is 3 to 6.

7. The method for producing a polynuclear poly (formylphenol) according to claim 5, characterized in that a polynuclear poly(alkoxymethylphenol), being a polynuclear polyphenol expressed by the aforementioned General Formula (8) where R is an *aliphatic hydrocarbon group that may have an* aromatic hydrocarbon group, hydroxyl group or [aliphatic hydrocarbon group that may have an] ether group, is obtained by causing a polynuclear polyphenol expressed by General Formula (10) to react with formaldehyde in the presence of an alkali catalyst and then causing the obtained polynuclear poly(hydroxymethylphenol) expressed by General Formula (11) to further react with an alcohol expressed by General Formula (12) specified below in the presence of an acid catalyst:

General Formula (10)

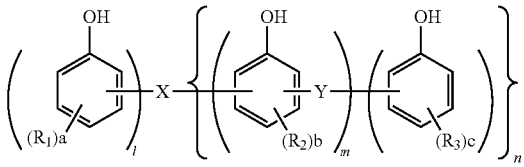

wherein $R_1$, $R_2$, $R_3$, a, b, c, l, m, n, X and Y indicate the same things represented by the corresponding symbols in General Formula (1), and at least one of the o-position and p-position of the hydroxyl group is not substituted; if m is 0, however, X is a trivalent to hexavalent bond group and l+n is 3 to 6;

General Formula (11)

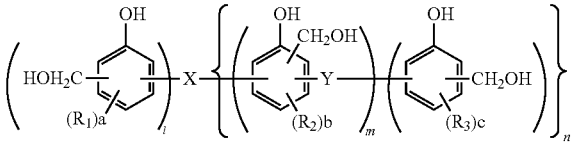

wherein $R_1$, $R_2$, $R_3$, a, b, c, l, m, n, X and Y indicate the same things represented by the corresponding symbols in General Formula (1), and the substituted position of the hydroxy methyl group corresponds to the o-position or p-position relative to the hydroxyl group. If m is 0, however, X is a trivalent to hexavalent bond group and l+n is 3 to 6;

R—OH General Formula (12)

wherein R represents an *aliphatic hydrocarbon group that may have an* aromatic hydrocarbon group, hydroxyl group or [aliphatic hydrocarbon group that may have an] ether group.

* * * * *

UNITED STATES PATENT AND TRADEMARK OFFICE

CERTIFICATE OF CORRECTION

PATENT NO. : RE43,067 E
APPLICATION NO. : 12/984215
DATED : January 3, 2012
INVENTOR(S) : Akira Yoshitomo, Tatsuya Iwai and Kentaro Watanabe It is certified that error appears in the above-identified patent and that said Letters Patent is hereby corrected as shown below:

1. At Column 3, Line 36 (Approx.), Change "group." to --group;--.
2. At Column 3, Line 43 (Approx.), After "or" insert --a--.
3. At Column 3, Line 49-55,

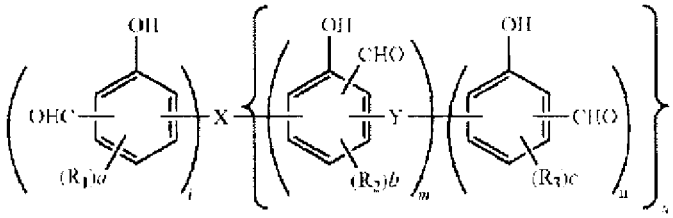

Change "  "

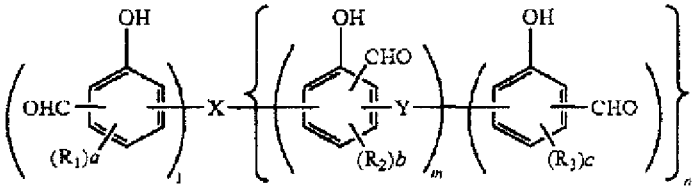

to --  --.

4. At Column 5, Line 65, Change "an]ether group." to --an] ether group;--.
5. At Column 6, Line 24 (Approx.), Change "(formylphenol)according" to --(formylphenol) according--.

Signed and Sealed this
Thirty-first Day of July, 2012

David J. Kappos

David J. Kappos
*Director of the United States Patent and Trademark Office*

6. At Column 6, Line 39-45 (Approx.),

Change “ 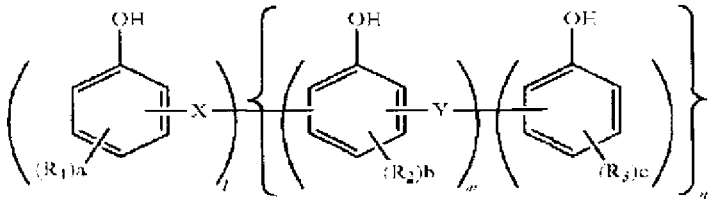 ”

to -- 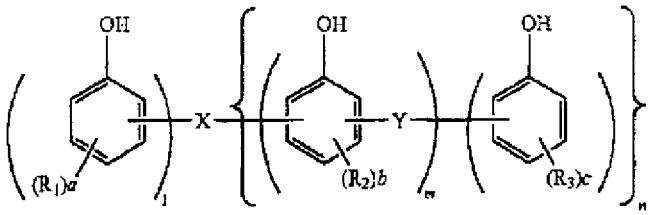 --.

7. At Column 6, Line 58-63 (Approx.),

Change “ 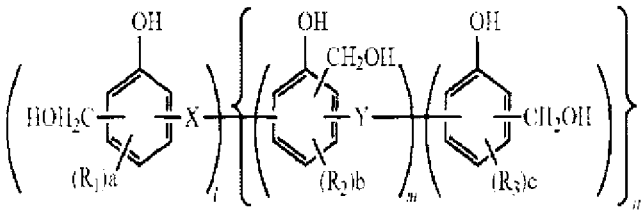 ”

to -- 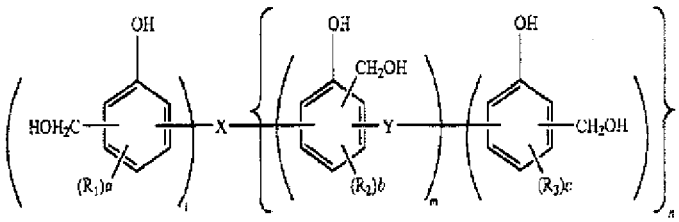 --.

8. At Column 7, Line 5 (Approx.), Change “(formylphenol)according” to --(formylphenol) according--.

9. At Column 8, Line 12, Change “propandiyl;” to --propanediyl;--.

10. At Column 8, Line 23, Change “[4.4.0.1$^{2,5}$0.1$^{7,10}$]” to --[4.4.0.1$^{2,5}$.1$^{7,10}$]--.

11. At Column 8, Line 59, Change “[4.4.0.1$^{2,5}$0.1$^{7,10}$]” to --[4.4.0.1$^{2,5}$.1$^{7,10}$]--.

12. At Column 10, Line 1, Change “4,4'dicarbonyl” to --4,4'-dicarbonyl--.

13. At Column 11, Line 16 (Approx.), Change “[4.4.0.1$^{2,5}$0.1$^{7,10}$]” to --[4.4.0.1$^{2,5}$.1$^{7,10}$]--.

14. At Column 14, Line 15-22 (Approx.),

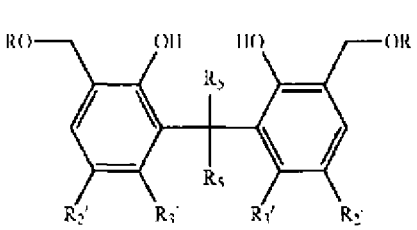

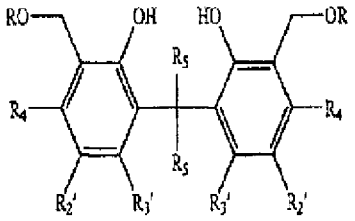

Change “ ” to -- --.

15. At Column 15, Line 35, Change “hydroxyphen yl]” to --hydroxyphenyl]--.
16. At Column 15, Line 64, Change “alicylcic” to --alicyclic--.
17. At Column 18, Line 3, Change “alicylcic” to --alicyclic--.
18. At Column 18, Line 54 (Approx.), Change “orb” to --or b--.
19. At Column 20, Line 22-23 (Approx.), Change “methy 1” to --methyl--.
20. At Column 21, Line 44 (Approx.), Change “$R_1$” to --$R_1$,--.
21. At Column 23, Line 24 (Approx.), Change “hydrox ymethyl” to --hydroxymethyl--.
22. At Column 23, Line 27 (Approx.), Change “methox ymethyl” to --methoxymethyl--.
23. At Column 23, Line 31 (Approx.), Change “butoxym ethyl” to --butoxymethyl--
24. At Column 24, Line 12 (Approx.), Change “hydrox ymethyl” to --hydroxymethyl--.
25. At Column 24, Line 18, Change “methy 1” to --methyl--.
26. At Column 24, Line 67 (Approx.), Below “Chemical Formula 16” insert
--[First reaction (reaction with hexamethylene tetramine)][Second reaction (hydrolysis)]--.
27. At Column 25, Line 14, Change “monochloro acetic” to --monochloroacetic--.
28. At Column 30, Line 66, Change “opposition” to --o-position--.
29. At Column 31, Line 15, Change “opposition” to --o-position--.
30. At Column 31, Line 31-32 (Approx.), Change “hydrox y methyl” to --hydroxymethyl--.
31. At Column 34, Line 21 (Approx.), Change “chromatograph” to --chromatography--.
32. At Column 34, Line 63 (Approx.), Change “ (M H)⁻ ” to --(M-H)⁻--.
33. At Column 35, Line 63 (Approx.), Change “ (M H)⁻ ” to --(M-H)⁻--.
34. At Column 37, Line 13, Change “ (M H)⁻ ” to --(M-H)⁻--.
35. At Column 38, Line 4-5 (Approx.), Change “methy 1” to --methyl--.
36. At Column 38, Line 14 (Approx.), Change “hydrox ymethyl” to --hydroxymethyl--.
37. At Column 39, Line 24 (Approx.), Change “hydrox ymethyl” to --hydroxymethyl--.
38. At Column 43, Line 3, In Claim 5, change “group,” to --group;--.
39. At Column 44, Line 52, In Claim 7, change “group. If” to --group; if--.